United States Patent [19]
Keating et al.

[11] Patent Number: 5,599,673
[45] Date of Patent: Feb. 4, 1997

[54] LONG QT SYNDROME GENES

[75] Inventors: Mark T. Keating; Mark E. Curran; Qing Wang, all of Salt Lake City, Utah

[73] Assignee: University of Utah Research Foundation, Salt Lake City, Utah

[21] Appl. No.: 401,512

[22] Filed: Mar. 9, 1995

[51] Int. Cl.$^6$ ............................. C12Q 1/68; C12P 19/34; C07H 21/04; C12N 15/00
[52] U.S. Cl. ........................ 435/6; 435/91.1; 435/91.2; 436/94; 536/23.1; 536/23.5; 536/24.3; 536/24.31; 536/24.33; 536/25.3; 536/25.32; 935/3; 935/5; 935/77; 935/78
[58] Field of Search ........................ 435/6, 91.1, 91.2, 435/183; 536/23.1, 24.3, 24.31, 24.33, 25.3, 25.32, 23.5; 935/1, 3, 5, 8, 16, 76, 77, 78; 436/94

[56] References Cited

U.S. PATENT DOCUMENTS

| | | | |
|---|---|---|---|
| 4,800,159 | 1/1989 | Mullis et al. | 435/172.3 |
| 5,364,790 | 11/1994 | Atwood et al. | 435/288 |

OTHER PUBLICATIONS

Sommer and Tautz, "Minimal homology requirements for PCR primers", *Nucleic Acids Research,* vol. 17, No. 16, 1989, p. 6749.
Keating, "Genetic approaches to cardiovascular disease: Supravalvular aortic stenosis, Williams syndrome, and long–QT syndrome", *Circulation,* vol. 92, No. 1, 1995, pp. 142–147; abstract only.
Q. Wang et al. "SCN5A Mutations Associated with an Inherited Cardiac Arrhythmia, Long QT Syndrome", *Cell* 80:805–811 (1995).
M. E. Curran et al. "A Molecular Basis for Cardiac Arrhythmia: HERG Mutations Cause Long QT Syndrome", *Cell* 80:795–803 (1995).
M. Keating. "Linkage Analysis and Long QT Syndrome. Using Genetics to Study Cardiovascular Disease", *Circulation* 85:1973–1986 (1992).
M. Keating et al. "Consistent Linkage of the Long–QT Syndrome to the Harvey Ras–I Locus on Chromosome 11", *Am. J. Hum. Genet.* 49:1335–1339 (1991).
C. Jiang et al. "Two long QT syndrome loci map to chromosomes 3 and 7 with evidence for further heterogeneity", *Nature Genetics* 8:141–147 (1994).
J. Marx. "Rare Heart Disease Linked to Oncogene", *Science* 252:647 (1991).
M. Keating et al. "Linkage of a Cardiac Arrhythmia, the Long QT Syndrome, and the Harvey ras–1 Gene", *Science* 252:704–706 (1991).
M. Keating. "Evidence of Genetic Heterogeneity in the Long QT Syndrome", *Science* 260:1960–1962 (1993).
L. J. Ptácek et al. "Identification of a Mutation in the Gene Causing Hyperkalemic Periodic Paralysis", *Cell* 67:1021–1027 (1991).
A. L. George, Jr. et al. "Assignment of the human heart tetrodotoxin–resistant voltage-gated Na$^+$ channel α–subunit gene (SCN5A) to band 3p21", *Cytogenet. Cell Genet.* 68:67–70 (1995).
M. E. Gellens et al. "Primary structure and functional expression of the human cardiac tetrodotoxin–insensitive voltage–dependent sodium channel", *Proc. Natl. Acad. Sci. USA* 89:554–558 (1992).
M. Curran et al. "Locus Heterogeneity of Autosomal Dominant Long QT Syndrome", *J. Clin. Invest.* 92:799–803 (1993).
J. A. Towbin et al. "Evidence of Genetic Heterogeneity in Romano–Ward Long QT Syndrome. Analysis of 23 Families", *Circulation* 90:2635–2644 (1994).

Primary Examiner—Bradley L. Sisson
Attorney, Agent, or Firm—Venable, Baetjer, Howard & Civiletti, LLP

[57] ABSTRACT

The invention relates to the identification of the molecular basis of long QT syndrome. More specifically, the invention has identified that SCN5A and HERG cause long QT syndrome. Molecular variants of the SCN5A and HERG genes contribute to the syndrome. The analysis of these genes will provide an early diagnosis of subjects with long QT syndrome. The diagnostic methods comprise analyzing the nucleic acid sequences of the SCN5A or HERG genes of an individual to be tested and comparing them with the nucleic acid sequence of the native, nonvariant genes. Alternatively, the amino acid sequences of SCN5A or HERG may be analyzed for mutations which cause long QT syndrome. Presymptomatic diagnosis of long QT syndrome will enable practitioners to treat this disorder using existing medical therapy.

32 Claims, 22 Drawing Sheets

```
                              DNFNQQKKKLGGQ  DIFMTEEQKKYYNAMKKLGSKKPQKPIPRPLNKYQGFIFD
SCN5A
human heart muscle            .............  ........................................

SCN4A
human skeletal muscle         .............  ...................Q..I..MVY...........

SCN1A                         .....F.......  ..........................K.............
human brain                   .....F..K....  ...................A..F..MV.............

rat skeletal muscle           .....F.......  ...................Q..I..MVY.............

rat brain II                  .....F.......  ...................A..F..MV.............

rat brain I                   .....F.......  ...................G..F..MV.............

Fugu rubripes                 .....F.......  ...................Q..I..MV.............

Loligo opalescens             .......GA..S LEV..DD....K...N.Q...T.G..M.GF.IAEWM.H Loligo bleekiri               .K.SFL...YD.TYL.M.L.PT.QN...TL....T....TVK..K..C.AVVY.

Drosophila melanogaster       ....MLRRSIE.V LEM.L..S..H..T......R....V.K..I.HFLAMFY.

Heliothis virescens           ...E....AA.S LEM....D........M.....L.A....KWRP.AIV.F
```

FIG. 2

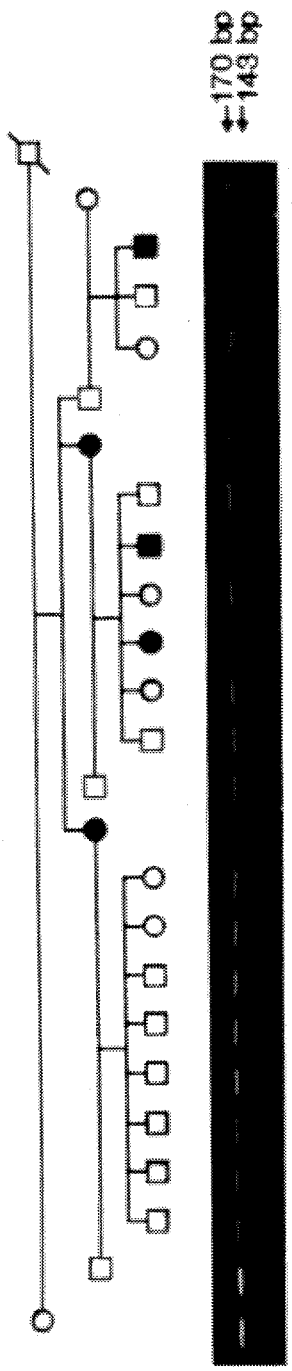
FIG. 10A
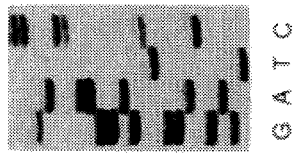
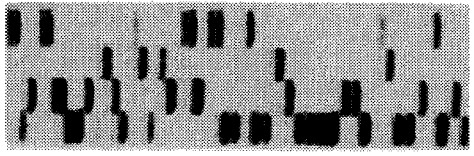
FIG. 10B

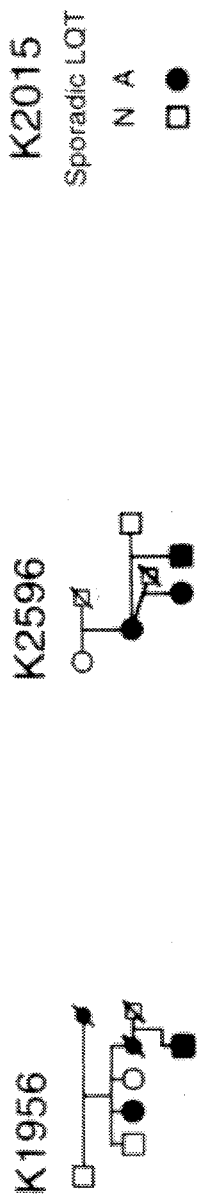
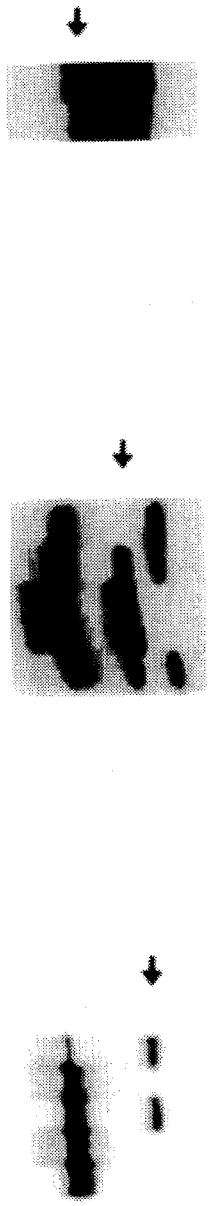
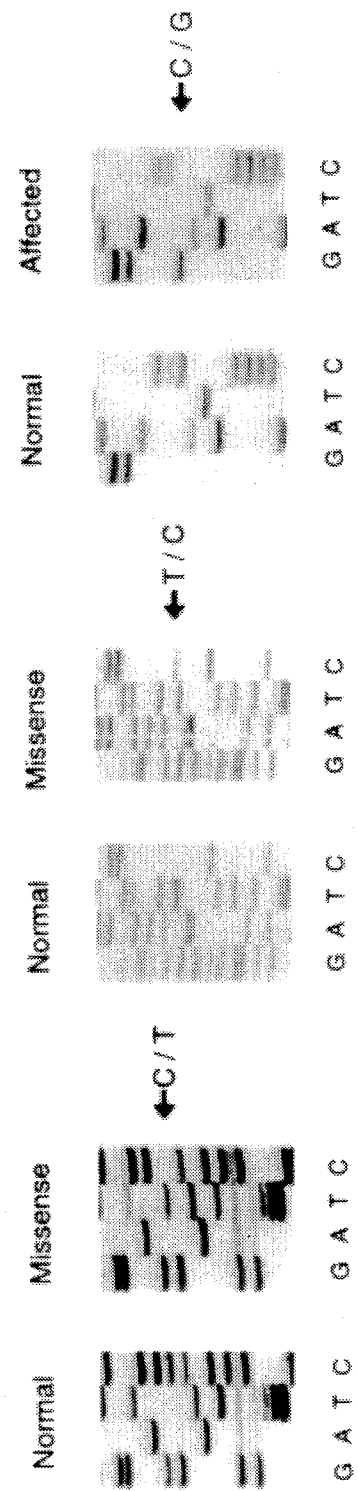

FIG. 12G

| | | | S5 | | | | SEQ ID NO.: |
|---|---|---|---|---|---|---|---|
| | | | GTG → V | | | | |
| | | | GCG ↗ | | | | |
| | L | I | A | H | W | L | |
| K1956 | L | L | V | H | W | L | 67 |
| H-Erg | L | L | A | H | W | L | 68 |
| M-Eag | L | L | A | H | W | K | 67 |
| R-Eag | L | V | A | H | W | L | 69 |
| Eag | L | V | A | H | W | L | 70 |
| Elk | L | L | A | H | W | L | 71 |
| | | | | | | | 72 |

FIG. 12H

| | | | S2 | | | | SEQ ID NO.: |
|---|---|---|---|---|---|---|---|
| | | | GAC → D | | | | |
| | | | AAC ↗ | | | | |
| | D | I | L | I | N | F | R |
| K2596 | D | L | L | I | D | F | R | 73 |
| H-Erg | D | L | L | I | N | F | R | 74 |
| M-Eag | D | L | V | V | N | F | H | 73 |
| R-Eag | D | L | V | V | N | F | H | 75 |
| Eag | D | L | L | I | N | F | H | 75 |
| Elk | D | L | L | I | N | F | R | 76 |

FIG. 12I

```
              c
              ↓
5'-CAT CCT GG // gtatggg-3"
```

| | | | | | AGC → S<br>GGC<br>\ / | | | SEQ ID<br>NO.: |
|---|---|---|---|---|---|---|---|---|
| | S | V | G | F | G | N | V | S | 77 |
| | ← Pore → | | | | | | | |
| K2269 | S | V | G | F | S | N | V | S | 78 |
| H-Erg | S | V | G | F | G | N | V | S | 77 |
| M-Eag | S | V | G | F | G | N | I | A | 79 |
| R-Eag | S | V | G | F | G | N | I | A | 79 |
| Eag | S | V | G | F | G | N | V | A | 80 |
| Elk | S | V | G | F | G | N | V | S | 77 |
| Shaker | T | V | G | Y | G | D | M | T | 81 |

LONG QT SYNDROME GENES

This application was made with Government support under Grant Nos. R01 HL48074, R01 HL33843, and R01 HL51618 funded by the National Institutes of Health, Bethesda, Md., and Grant No. M01 RR00064 from the U.S. Public Health Service.

BACKGROUND OF THE INVENTION

The present invention is directed to a process for the diagnosis and prevention of long QT syndrome (LQT). LQT is diagnosed in accordance with the present invention by analyzing the DNA sequences of the SCN5A and HERG genes of an individual to be tested and comparing the respective DNA sequences to the known DNA sequences of normal SCN5A and HERG genes. Alternatively, the SCN5A and HERG genes of an individual to be tested can be screened for mutations which cause LQT. Prediction of LQT will enable practitioners to prevent this disorder using existing medical therapy.

The publications and other materials used herein to illuminate the background of the invention or provide additional details respecting the practice, are incorporated by reference, and for convenience are respectively grouped in the appended List of References.

Although sudden death from cardiac arrhythmias is thought to account for 11% of all natural deaths, the mechanisms underlying arrhythmias are poorly understood (Kannel, 1987; Willich et al., 1987). Long QT syndrome (LQT) is an inherited cardiac arrhythmia that causes abrupt loss of consciousness, syncope, seizures and sudden death from ventricular tachyarrhythmias, specifically torsade de pointes and ventricular fibrillation (Ward, 1964; Romano, 1965; Schwartz et al., 1975; Moss et al., 1991). This disorder usually occurs in young, otherwise healthy individuals (Ward, 1964; Romano, 1965; Schwartz, 1975). Most LQT gene carriers manifest prolongation of the QT interval on electrocardiograms, a sign of abnormal cardiac repolarization (Vincent et al., 1992). The clinical features of LQT result from episodic cardiac arrhythmias, specifically torsade de pointes, named for the characteristic undulating nature of the electrocardiogram in this arrhythmia. Torsade de pointes may degenerate into ventricular fibrillation, a particularly lethal arrhythmia. Although LQT is not a common diagnosis, ventricular arrhythmias are very common; more than 300,000 United States citizens die suddenly every year (Kannel, et al., 1987; Willich et al., 1987) and, in many cases, the underlying mechanism may be aberrant cardiac repolarization. LQT, therefore, provides a unique opportunity to study life-threatening cardiac arrhythmias at the molecular level.

Autosomal dominant and autosomal recessive forms of this disorder have been reported. Autosomal recessive LQT (also known as Jervell-Lange-Nielson syndrome) has been associated with congenital neural deafness; this form of LQT is rare (Jervell and Lange-Nielson, 1957). Autosomal dominant LQT (Romano-Ward syndrome) is more common, and is not associated with other phenotypic abnormalities. A disorder very similar to inherited LQT can also be acquired, usually as a result of pharmacologic therapy (Schwartz et al., 1975; Zipes, 1987).

In 1991, the complete linkage between autosomal dominant LQT and a polymorphism at HRAS was reported (Keating et al., 1991a; Keating et al., 1991b). This discovery localized LQT1 to chromosome 11p15.5 and made presymptomatic diagnosis possible in some families. Autosomal dominant LQT was previously thought to be genetically homogeneous, and the first seven families that were studied were linked to 11p15.5 (Keating et al., 1991b). In 1993, it was found that there was locus heterogeneity for LQT (Benhorin et al, 1993; Curran et al., 1993b; Towbin et al., 1994). Two additional LQT loci were subsequently identified, LQT2 on chromosome 7q35–36 (nine families) and LQT3 on 3p21–24 (three families) (Jiang et al., 1994). Several families remain unlinked to the known loci, indicating additional locus heterogeneity for LQT. This degree of heterogeneity suggests that distinct LQT genes may encode proteins that interact to modulate cardiac repolarization and arrhythmia risk.

Although little is known about the physiology of LQT, the disorder is associated with prolongation of the QT interval on electrocardiograms, a sign of abnormal cardiac repolarization. This association suggests that genes encoding ion channels, or their modulators, are reasonable candidates for LQT. HRAS, which was localized to chromosome 11p15.5, was excluded as a candidate for LQT1 based on direct DNA sequence analyses (unpublished observations) and by linkage analyses (Roy et al., 1994). A neuroendocrine calcium channel gene (CACNL1A2; Chin et al., 1991; Seino et al., 1992) and a gene encoding a GTP-binding protein that modulates potassium channels (GNAI2; Weinstein et al., 1988; Magovcevic et al., 1992) became candidates for LQT3 based on their chromosomal location. Subsequent linkage analyses, however, have excluded these genes (Wang and Keating, unpublished data). A skeletal muscle chloride channel (CLCN1; Koch et al., 1992) and a cardiac muscarinic-acetylcholine receptor (CHRM2; Bonner et al., 1987) became candidates for LQT2 based on their chromosome 7q35–36 location, but subsequent linkage analyses have excluded these genes (Wang et al., submitted).

In theory, mutations in a cardiac sodium channel gene could cause LQT. Voltage-gated sodium channels mediate rapid depolarization in ventricular myocytes, and also conduct a small current during the plateau phase of the action potential (Attwell et at., 1979). Subtle abnormalities of sodium channel function (e.g., delayed sodium channel inactivation or altered voltage-dependence of channel inactivation) could delay cardiac repolarization, leading to QT prolongation and arrhythmias. In 1992, Gellens and colleagues cloned and characterized a cardiac sodium channel gene, SCN5A (Gellens et al., 1992). The structure of this gene was similar to other, previously characterized sodium channels, encoding a large protein of 2016 amino acids. These channel proteins contain four homologous domains (DI–DIV), each of which contains six putative membrane spanning segments (S1–S6). SCN5A was recently mapped to chromosome 3p21, making it an excellent candidate gene for LQT3 (George et al., 1995).

In 1994, Warmke and Ganetzky identified a novel human cDNA, human ether a-go-go related gene (HERG, Warmke and Ganetzky, 1994). HERG was localized to human chromosome 7 by PCR analysis of a somatic cell hybrid panel (Warmke and Ganetzky, 1994). The function of the protein encoded by HERG is not known, but it has predicted amino acid sequence homology to potassium channels. HERG was isolated from a hippocampal cDNA library by homology to the Drosophila ether a-go-go gene (eag), which encodes a calcium-modulated potassium channel (Bruggeman et al., 1993). HERG is not the human homolog of eag, however, sharing only ~50% amino acid sequence homology.

Evidence is presented here indicating that SCN5A is LQT3 and HERG is LQT2. Three families with mutations in SCN5A were identified and characterized and it was shown that in all three families there was complete linkage between LQT3 and SCN5A. For the HERG gene, new LQT families were identified and characterized and it was shown that all were linked to markers on chromosome 7q35–36, confirming the location of LQT2. Second, HERG was mapped to chromosome 7q35–36, making HERG a candidate gene for LQT2. Third, it was demonstrated that HERG is strongly expressed in the heart. Finally, six HERG mutations which cause LQT were identified; one of these mutations arose de novo.

SUMMARY OF THE INVENTION

The present invention demonstrates the molecular basis of long QT syndrome. More specifically, the present invention has determined that molecular variants of either one of the SCN5A or the HERG genes cause or are involved in the pathogenesis of LQT. Genotypic analyses show that SCN5A is completely linked to LQT3 in three unrelated families. The same intragenic deletion of SCN5A was identified in affected members of two of these families. These deletions disrupted sequences within a region of known importance for sodium channel inactivation, suggesting a likely cellular mechanism for chromosome 3-linked LQT. Genotypic analyses show that HERG is also linked to LQT2 in six families. The mutations found in these families include two intragenic deletions, one splice-donor mutation and three missense mutations. Analysis of the SCN5A and HERG genes will provide an early diagnosis of subjects with LQT. The diagnostic method comprises analyzing the DNA sequence of the SCN5A and/or HERG gene of an individual to be tested and comparing it with the DNA sequence of the native, non-variant gene. In a second embodiment, the SCN5A and/or HERG gene of an individual to be tested is screened for mutations which cause LQT. The ability to predict LQT will enable physicians to prevent the disease with medical therapy such as beta blocking agents.

BRIEF DESCRIPTION OF THE FIGURES

FIG. 2. Amino acid sequence homology of the cytoplasmic region between DIII and DIV of sodium channels. Sequences were obtained from GDB.

18)-3', Intron III, 5'-CCTGGgtatgg(SEQ ID NO: 19) . . . ctccagGGAAG(SEQ ID NO:20)-3'.

Figures 10C, 11C:

FIGS. 10A–10C. HERG intragenic deletions associated with LQT in two families. Pedigree structure of K2287 (FIG. 10A), results of PCR amplification using primer pair 1–9 (FIG. 10A), results of DNA sequencing of normal and mutant K2287 HERG genes (FIG. 10B), and the effect of the deletion on predicted structure of HERG protein (FIG. 10C) are shown. Note that an aberrant fragment of 143 bp is observed in affected members of this kindred, indicating the presence of a disease-associated intragenic deletion. DNA sequence of normal and aberrant PCR products defines a 27 bp deletion (ΔI500–F508). This mutation causes an in-frame deletion of 9 amino acids in the third membrane spanning domain (S3). Deleted sequences are indicated.

Figure 11A:
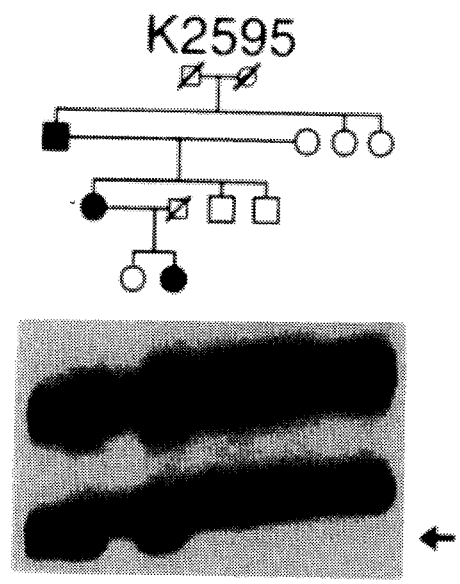
Figure 11B:
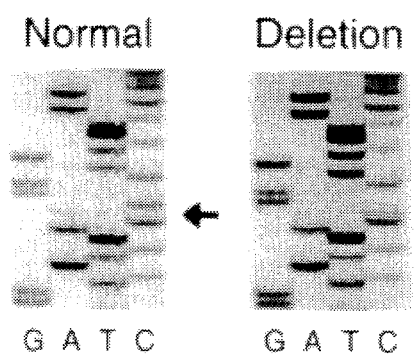

FIGS. 11A–11C. Pedigree structure of K2595 is shown (FIG. 11A). Deceased individuals are indicated by a slash. The result of SSCP analyses using primer pair 1–9 are shown beneath each individual (FIG. 11A). Note that an aberrant SSCP conformer cosegregates with the disease in this family. DNA sequence shows a single base-pair deletion (Δ1261) (FIG. 11B). This deletion results in a frameshift followed by a stop codon 12 amino acids downstream (FIG. 11C). The deleted nucleotide is indicated with an arrow.

FIGS. 12A–12I. HERG point mutations identified in three LQT kindreds. Pedigree structure of K1956 (FIG. 12A), K2596 (FIG. 12C) and K2015 (FIG. 12E) are shown. Below each pedigree, the results of SSCP analyses with primer pair 5–11 (K1956) (FIG. 12B), primer pair 1–9 (K2596) (FIG. 12D) and primer pair 4–12 (K2015) (FIG. 12F) are shown. Aberrant SSCP conformers cosegregate with the disease in each kindred. DNA sequence analyses of the normal and aberrant conformers reveals a C to T substitution at position 1682 in K1956. This mutation results in substitution of valine for a highly conserved alanine residue at codon 561 (A561V) (FIG. 12G). Analyses of K2596 reveals an A to G substitution at position 1408 (T to C substitution on the anti-sense strand is shown) (FIG. 12D). This mutation results in substitution of aspartic acid for a conserved asparagine in the second transmembrane domain (N470D) (FIG. 12H). Analyses of K2015 reveals a G to C substitution (C to G substitution on the anti-sense strand is shown) (FIG. 12F). This mutation occurs in the splice-donor sequence of intron III (FIG. 12I). Coding sequences are upper case and intronic sequences are lower case. Note that the G to C substitution disrupts the splice-donor site. (HERG, M-eag, elk, Warmke and Ganetzky, 1994; R-eag; Ludwig et al., 1994).

Figure 13A:
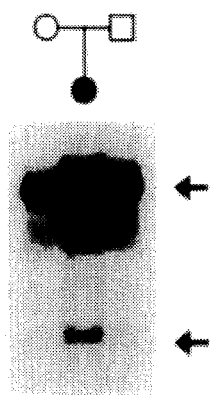
Figure 13B:
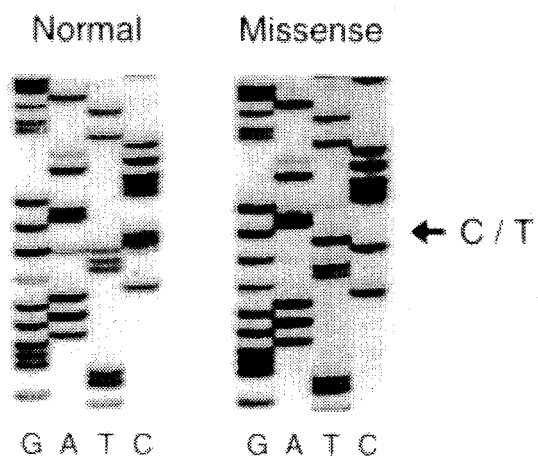

FIGS. 13A–13C. De novo mutation of HERG in a sporadic case of LQT. Pedigree structure of K2269 (FIG. 13A) and SSCP analyses (primer pair 14–16) (FIG. 13A) showing an aberrant conformer in a sporadic case of LQT. DNA sequence analyses identified a G to A substitution at position 1882 of the cDNA sequence (C to T substitution on the antisense-strand is shown) (FIG. 13B). Note that this mutation results in the substitution of a serine for a highly conserved glycine residue at codon 628 (G628S) (FIG. 13C). This amino acid sequence is known to be critical for potassium ion selectivity.

FIG. 14. Northern blot analysis of HERG mRNA showing strong expression in the heart. A Northern blot (Clonetech, poly A$^+$RNA, 2 mg/lane) was probed using an HERG cDNA containing nucleotides 679 to 2239 of the coding sequence. Two cardiac mRNAs of ~4.1 and 4.4 kb are indicated. Background in mRNA extracted from lung was high, but no specific bands were identified.

Figure 15:
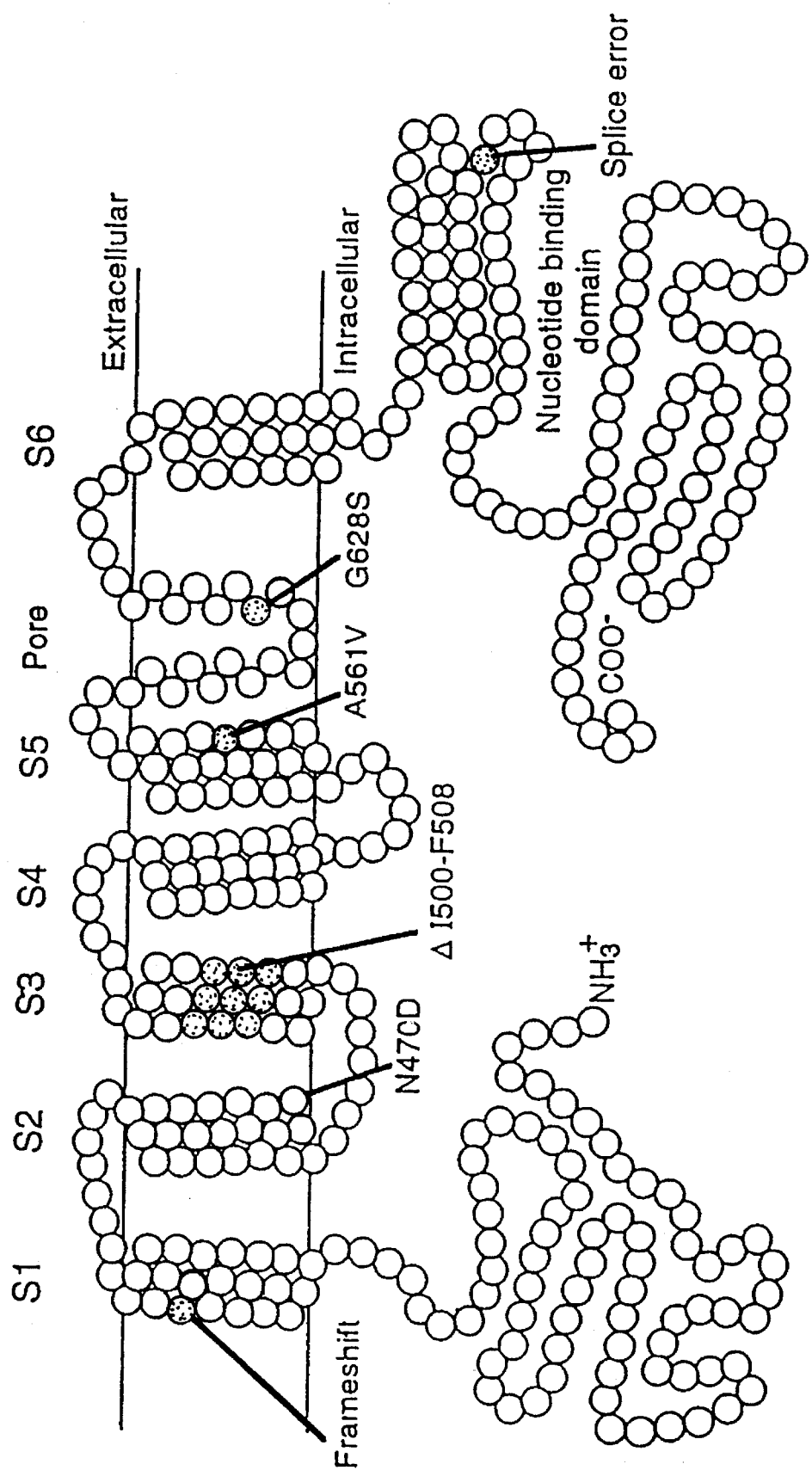

FIG. 15. Schematic representation of the predicted topology of the protein encoded by HERG and the location of LQT-associated mutations. For simplicity, not all amino acids are shown. SSCP analyses identified HERG mutations in four of the 14 chromosome 7-linked kindreds.

DETAILED DESCRIPTION OF THE INVENTION

The present invention is directed to the determination that LQT maps to both the SCN5A and HERG genes and that molecular variants of these genes cause or are involved in the pathogenesis of LQT. More specifically, the present invention relates to mutations in the SCN5A and HERG genes and their use in the diagnosis of LQT. The present invention is further directed to methods of screening humans for the presence of SCN5A and HERG gene variants which cause LQT. Since LQT can now be detected earlier (i.e., before symptoms appear) and more definitively, better treatment options will be available in those individuals identified as having LQT.

The present invention provides methods of screening the SCN5A and HERG genes to identify mutations. Such methods may further comprise the step of amplifying a portion of the SCN5A or HERG gene, and may further include a step of providing a set of polynucleotides which are primers for amplification of said portion of the SCN5A or HERG gene. The method is useful for identifying mutations for use in either diagnosis of LQT or prognosis of LQT.

Long QT syndrome is an inherited disorder that causes sudden death from cardiac arrhythmias, specifically torsade de pointes and ventricular fibrillation. LQT was previously mapped to three loci: LQT1 on chromosome 11p15.5, LQT2 on 7q35-36 and LQT3 on 3p21-24. It is a discovery of the present invention that there is a genetic linkage between LQT3 and polymorphisms within SCN5A, the cardiac sodium channel gene. It is also a discovery of the present invention that there is a genetic linkage between LQT2 and polymorphisms within HERG. SSCP and DNA sequence analyses reveal identical intragenic deletions of SCN5A in affected members of two unrelated LQT families. The deleted sequences reside in a region that is important for channel inactivation. These data suggest that mutations in SCN5A cause chromosome 3-linked LQT, and indicate a likely cellular mechanism for this disorder. SSCP and DNA sequence analyses revealed two distinct intragenic deletions of HERG in two affected individuals. One mutation caused a 27 bp deletion beginning at position 1498. This deletion disrupts the third membrane spanning domain (S3) of HERG. The other deletion was of a single base at position 1261. This results in a frameshift in sequences encoding the first membrane spanning domain (S1), leading to a new stop codon within 12 amino acids. Similar analyses also found three distinct missense mutations in three other affected individuals and a splice-donor mutation in another affected individual.

Proof that the SCN5A and HERG genes are involved in causing LQT is obtained by finding sequences in DNA extracted from affected kindred members which create abnormal SCN5A or HERG gene products or abnormal levels of the gene products. Such LQT susceptibility alleles will co-segregate with the disease in large kindreds. They will also be present at a much higher frequency in non-kindred individuals with LQT than in individuals in the general population. The key is to find mutations which are serious enough to cause obvious disruption to the normal function of the gene product. These mutations can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

According to the diagnostic and prognostic method of the present invention, alteration of the wild-type SCN5A or HERG gene is detected. In addition, the method can be performed by detecting the wild-type SCN5A or HERG gene and confirming the lack of a cause of LQT as a result of these two loci. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues and are not inherited in the germline. Germline mutations can be found in any of a body's tissues and are inherited. Point mutational events may occur in regulatory regions, such as in the promoter of the gene, leading to loss or diminution of expression of the mRNA. Point mutations may also abolish proper RNA processing, leading to loss of expression of the SCN5A or HERG gene product, or to a decrease in mRNA stability or translation efficiency.

The presence of LQT may be ascertained by testing any tissue of a human mutations of the SCN5A and/or HERG genes. For example, a person who has inherited a germline SCN5A or HERG mutation would be prone to develop LQT. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the SCN5A and/or HERG genes. Alteration of a wild-type SCN5A or HERG allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation.

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of LQT cases. Southern blots displaying hybridizing fragments (differing in length from control DNA when probed with sequences near or including the SCN5A or HERG loci) indicate a possible mutation. If restriction enzymes which produce very large restriction fragments are used, then pulsed field gel electrophoresis (PFGE) is employed.

Detection of point mutations may be accomplished by molecular cloning of the SCN5A or HERG alleles and sequencing the alleles using techniques well known in the art.

There are six well known methods for a more complete, yet still indirect, test for confirming the presence of a susceptibility allele: 1) single stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Comber et al., 1983); 5) the use of proteins which recognize nucleotide mismatches, such as the E. coli mutS protein (Modrich, 1991 ); and 6) allele-specific PCR (Rano and Kidd, 1989). For allele-specific PCR, primers are used which hybridize at their 3' ends to a particular SCN5A or HERG mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type SCN5A or HERG gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the SCN5A or HERG gene can also be detected using Southern hybridization, especially if the changes are gross rearrangements, such as deletions and insertions.

DNA sequences of the SCN5A or HERG gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified SCN5A or HERG sequences can be perforated, for example, on a nylon filter. Hybridization to a particular probe under stringent hybridization conditions indicates the presence of the same mutation in the tissue as in the allele-specific probe.

The most definitive test for mutations in a candidate locus is to directly compare genomic SCN5A or HERG sequences from patients with those from a control population. Alternatively, one could sequence messenger RNA after amplification, e.g., by PCR, thereby eliminating the necessity of determining the exon structure of the candidate gene.

Mutations from patients falling outside the coding region of SCN5A or HERG can be detected by examining the non-coding regions, such as introns and regulatory sequences near or within the genes. An early indication that mutations in noncoding regions are important may come from Northern blot experiments that reveal messenger RNA molecules of abnormal size or abundance in patients as compared to control individuals.

Alteration of SCN5A or HERG mRNA expression can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type SCN5A or HERG protein. For example, monoclonal antibodies immunoreactive with SCN5A or HERG can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered SCN5A or HERG protein can be used to detect alteration of wild-type SCN5A or HERG genes. Functional assays, such as protein binding determinations, can be used. In addition, assays can be used which detect SCN5A or HERG biochemical function. Finding a mutant SCN5A or HERG gene product indicates alteration of a wild-type SCN5A or HERG gene.

Mutant SCN5A or HERG genes or gene products can also be detected in other human body samples, such as serum, stool, urine and sputum. The same techniques discussed above for detection of mutant genes or gene products in tissues can be applied to other body samples. By screening such body samples, a simple early diagnosis can be achieved for LQT.

The primer pairs of the present invention are useful for determination of the nucleotide sequence of a particular SCN5A or HERG allele using PCR. The pairs of single-stranded DNA primers can be annealed to sequences within or surrounding the SCN5A or HERG gene on chromosomes 3 or 7 respectively in order to prime amplifying DNA synthesis of the gene itself. A complete set of these primers allows synthesis of all of the nucleotides of the gene coding sequences, i.e., the exons. The set of primers preferably allows synthesis of both intron and exon sequences. Allele-specific primers can also be used. Such primers anneal only to particular SCN5A or HERG mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from SCN5A or HERG sequences or sequences adjacent to SCN5A or HERG, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequences of SCN5A (Gellens et al., 1992) and HERG (Warmke and Ganetzky, 1994), design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the SCN5A or HERG gene or mRNA using other techniques.

It has been discovered that individuals with the wild-type SCN5A and HERG genes do not have LQT. However, mutations which interfere with the function of the SCN5A or HERG gene products are involved in the pathogenesis of LQT. Thus, the presence of an altered (or a mutant) SCN5A or HERG gene which produces a protein having a loss of function, or altered function, directly causes LQT which increases the risk of cardiac arrhythmias. In order to detect an SCN5A or HERG gene mutation, a biological sample is prepared, and analyzed for a difference between the sequence of the allele being analyzed and the sequence of the wild-type allele. Mutant SCN5A or HERG alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele. The mutations, especially those which lead to an altered function of the protein, are then used for the diagnostic and prognostic methods of the present invention.

Definitions

The present invention employs the following definitions:

"Probes". Polynucleotide polymorphisms associated with SCN5A and HERG alleles which predispose to LQT are detected by hybridization with a polynucleotide probe which forms a stable hybrid with that of the target sequence, under stringent to moderately stringent hybridization and wash conditions. If it is expected that the probes will be perfectly complementary to the target sequence, stringent conditions will be used. Hybridization stringency may be lessened if some mismatching is expected, for example, if variants are expected with the result that the probe will not be completely complementary. Conditions are chosen which rule out non-specific/adventitious bindings, that is, which minimize noise. Since such indications identify neutral DNA polymorphisms as well as mutations, these indications need further analysis to demonstrate detection of an SCN5A or HERG susceptibility allele.

Probes for SCN5A or HERG alleles may be derived from the sequences of the SCN5A or HERG region or their cDNAs. The probes may be of any suitable length, which span all or a portion of the SCN5A or HERG region, and which allow specific hybridization to the region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding SCN5A or HERG are preferred as probes. The probes may also be used to determine whether mRNA encoding SCN5A or HERG is present in a cell or tissue.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C,, and preferably in excess of 45° C. Stringent salt conditions will ordinarily be less than 1000 mM, typically less than 500 mM, and preferably less than 200 mM. However, the combination of parameters is much more important than the measure of any single parameter. See, e.g., Wetmur & Davidson, 1968.

Probe sequences may also hybridize specifically to duplex DNA under certain conditions to form triplex or other higher order DNA complexes. The preparation of such probes and suitable hybridization conditions are well known in the art.

Preparation of Recombinant or Chemically Synthesized Nucleic Acids; Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage & Carruthers, 1981 or the triester method according to Matteucci et al., 1981, and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example, in Sambrook et al., 1989 or Ausubel et al., 1992. An appropriate promoter and other necessary vector sequences will be selected so as to be functional in the host, and may include, when appropriate, those naturally associated with SCN5A or HERG genes. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, Cold Spring Harbor, N.Y. (1983).

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the SCN5A or HERG nucleic acids or portions thereof in vectors or other expression vehicles in compatible prokaryotic or eukaryotic host cells. The most commonly used prokaryotic hosts are strains of *Escherichia coli,* although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), 1979. Examples of commonly used mammalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of SCN5A and HERG polypeptides.

The probes and primers based on the SCN5A and HERG gene sequences disclosed herein are used to identify homologous SCN5A and HERG gene sequences and proteins in other species. These gene sequences and proteins are used in the diagnostic/prognostic, therapeutic and drug screening methods described herein for the species from which they have been isolated.

Methods of Use: Nucleic Acid Diagnosis and Diagnostic Kits

In order to detect the presence of an SCN5A or HERG allele predisposing an individual to LQT, a biological sample such as blood is prepared and analyzed for the presence or absence of susceptibility alleles of SCN5A or HERG. In order to detect the presence of LQT or as a prognostic indicator, a biological sample is prepared and analyzed for the presence or absence of mutant alleles of SCN5A and/or HERG. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant SCN5A or HERG sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 3 or 7. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal front the labeled moiety. A number of these variations are reviewed in, e.g., Matthews & Kricka, 1988; Landegren et al., 1988; Mittlin, 1989; U.S. Pat. No. 4,868,105; and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al., 1986.

Two-step label amplification methodologies are known in the art. These assays work on the principle that a small ligand (such as digoxigenin, biotin, or the like) is attached to a nucleic acid probe capable of specifically binding SCN5A or HERG. Allele specific probes are also contemplated within the scope of this example and exemplary allele specific probes include probes encompassing the predisposing mutations of this patent application.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting SCN5A and/or HERG. Thus, in one example to detect the presence of SCN5A or HERG in a cell sample, more than one probe complementary to the gene is employed and in particular the number of different probes is alternatively two, three, or five different nucleic acid probe sequences. In another example, to detect the presence of mutations in the SCN5A or HERG gene sequence in a patient, more than one probe complementary to these genes is employed where the cocktail includes probes capable of binding to the allele-specific mutations identified in populations of patients with alterations in SCN5A or HERG. In this embodiment, any number of probes can be used, and will preferably include probes corresponding to the major gene mutations identified as predisposing an individual to LQT.

Methods of Use: Peptide Diagnosis and Diagnostic Kits

The presence of LQT can also be detected on the basis of the alteration of wild-type SCN5A or HERG polypeptide. Such alterations can be determined by sequence analysis in accordance with conventional techniques. More preferably, antibodies (polyclonal or monoclonal) are used to detect differences in, or the absence of SCN5A or HERG peptides. Techniques for raising and purifying antibodies are well known in the art and any such techniques may be chosen to achieve the preparations claimed in this invention. In a preferred embodiment of the invention, antibodies will immunoprecipitate SCN5A or HERG proteins from solution as well as react with these proteins on Western or immunoblots of polyacrylamide gels. In another preferred embodiment, antibodies will detect SCN5A or HERG proteins in paraffin or frozen tissue sections, using immunocytochemical techniques.

Preferred embodiments relating to methods for detecting SCN5A or HERG or their mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

Methods of Use: Gene Therapy

According to the present invention, a method is also provided of supplying wild-type SCN5A or HERG function to a cell which carries mutant SCN5A or HERG alleles. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner.

As generally discussed above, the SCN5A or HERG gene or fragment, where applicable, may be employed in gene therapy methods in order to increase the amount of the expression products of such genes in cells. It may also be useful to increase the level of expression of a given LQT gene even in those heart cells in which the mutant gene is expressed at a "normal" level, but the gene product is not fully functional.

Gene therapy would be carried out according to generally accepted methods, for example, as described by Friedman, 1991. Cells from a patient would be first analyzed by the diagnostic methods described above, to ascertain the production of SCN5A or HERG polypeptide in the cells. A virus or plasmid vector (see further details below), containing a copy of the SCN5A or HERG gene linked to expression control elements and capable of replicating inside the cells, is prepared. Suitable vectors are known, such as disclosed in U.S. Pat. No. 5,252,479 and PCT published application WO 93/07282. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990), herpesviruses including HSV and EBV (Margolskee, 1992; Johnson et al., 1992; Fink et at., 1992; Breakfield and Geller, 1987; Freese et al., 1990), and retroviruses of avian (Brandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Constantini and Lacy, 1981); membrane fusion-mediated transfer via liposomes (Felgner et al., 1987; Wang and Huang, 1989; Kaneda et al., 1989; Stewart et al., 1992; Nabel et al., 1990; Lim et al., 1992); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1991a; Curiel et al., 1991b).

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Gene transfer techniques which target DNA directly to heart tissue is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follows: patients who carry an SCN5A or HERG susceptibility allele are treated with a gene delivery vehicle such that some or all of their heart precursor cells receive at least one additional copy of a functional normal SCN5A or HERG allele. In this step, the treated individuals have reduced risk of LQT to the extent that the effect of the susceptible allele has been countered by the presence of the normal allele.

Methods of Use: Transformed Hosts

Animals for testing therapeutic agents can be selected after mutagenesis of whole animals or after treatment of germline cells or zygotes. Such treatments include insertion of mutant SCN5A or HERG alleles, usually from a second animal species, as well as insertion of disrupted homologous genes. Alternatively, the endogenous SCN5A or HERG gene(s) of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the presence of LQT must be assessed. If the test substance prevents or suppresses the appearance of LQT, then the test substance is a candidate therapeutic agent for treatment of LQT. These animal models provide an extremely important testing vehicle for potential therapeutic products.

Two strategies have been utilized herein to identify LQT genes, a candidate gene approach and positional cloning. Positional information is now available for three LQT loci with LQT1 having been mapped to chromosome 11p15.5 (Keating et al., 1991a; Keating et al., 1991b), LQT2 to 7q35–36 and LQT3 to 3p21–24 (Jiang et al 1994). The candidate gene approach relies on likely mechanistic hypotheses based on physiology. Although little is known about the physiology of LQT, the disorder is associated with prolongation of the QT interval on electrocardiograms, a sign of abnormal cardiac repolarization. This association suggests that genes encoding ion channels, or their modulators, are reasonable candidates for LQT. This hypothesis is now supported by the discovery that chromosome 7-linked LQT results from mutations in HERG, a putative cardiac potassium channel gene. A neuroendocrine calcium channel gene (CACNL1A2; Chin et al., 1991; Seino et al., 1992) and a gene encoding a GTP-binding protein that modulates potassium channels (GNAI2; Weinstein et al., 1988; Magovcevic et al., 1992) became candidates for LQT3 based on their chromosomal location. Subsequent linkage analyses, however, have excluded these genes (Wang and Keating, unpublished data).

In theory, mutations in a cardiac sodium channel gene could cause LQT. Voltage-gated sodium channels mediate rapid depolarization in ventricular myocytes, and also conduct a small current during the plateau phase of the action potential (Attwell et al., 1979). Subtle abnormalities of sodium channel function (e.g., delayed sodium channel inactivation or altered voltage-dependence of channel inactivation) could delay cardiac repolarization, leading to QT prolongation and arrhythmias. In 1992, Gellens and colleagues cloned and characterized a cardiac sodium channel gene, SCN5A (Gellens et al., 1992). The structure of this gene was similar to other, previously characterized sodium channels, encoding a large protein of 2016 amino acids. These channel proteins contain four homologous domains (DI–DIV), each of which contains six putative membrane spanning segments (S1–S6). SCN5A was recently mapped to chromosome 3p21, making it an excellent candidate gene for LQT3 (George et al., 1995).

Figure 1A:
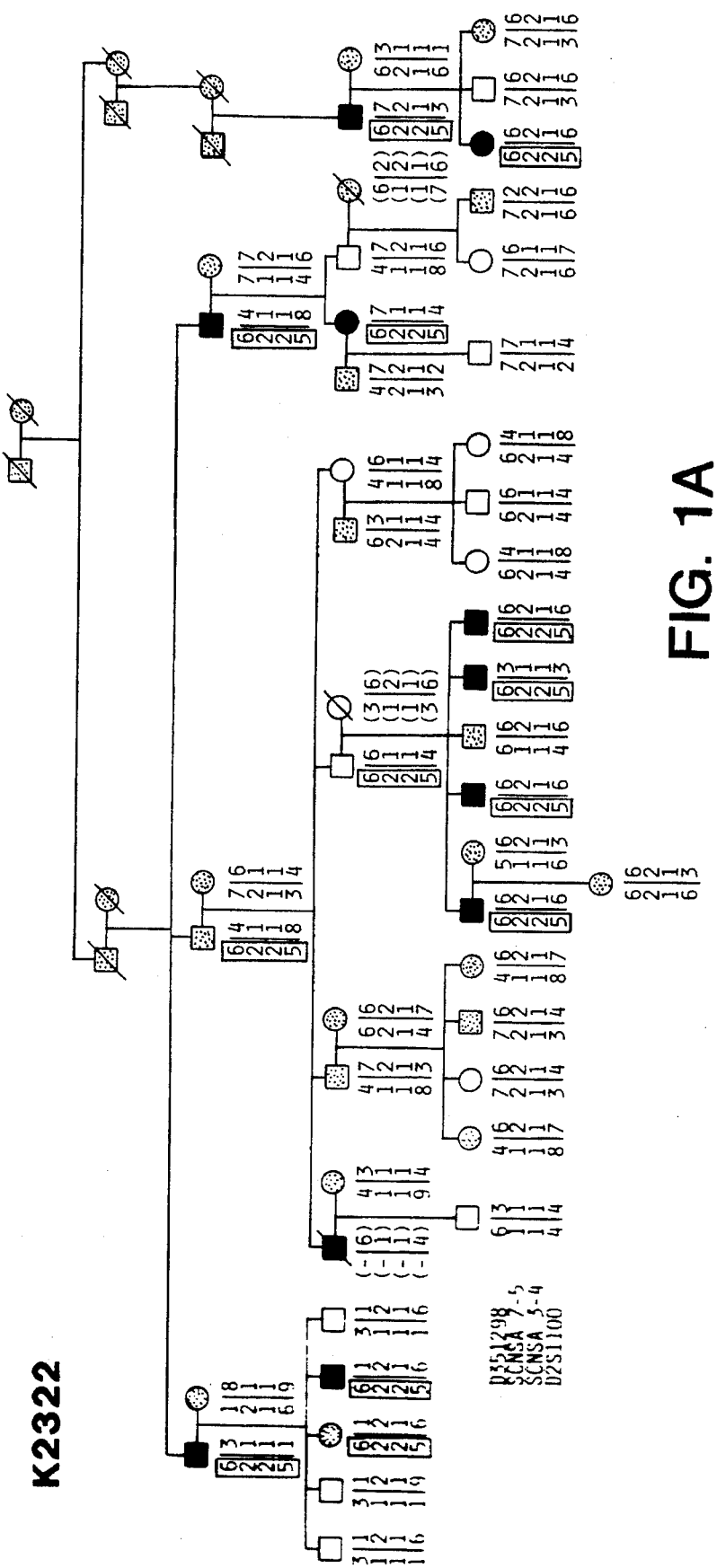
FIGS. 1A, 1B and 1C. Genetic linkage of SCN5A and LQT3. Pedigree structure and genotypic analyses of LQT kindreds 2322 (FIG. 1A), 2171 (FIG. 1B), and 2321 (FIG. 1C). Individuals with the characteristic features of LQT, including prolongation of the QT interval on electrocardiogram and a history of syncope or aborted sudden death are indicated by filled circles (females) or squares (males). Unaffected individuals are indicated by empty symbols, and individuals with an equivocal phenotype are stippled. Deceased individuals are indicated by a slash. The results of genotypic analyses are shown below each symbol. Genotypes for the following LQT3-linked polymorphic markers are shown (telomere to centromere): D3S1298, SCN5A 7–8, SCN5A 3–4, and D3S1100. Haplotypes cosegregating with the disease are indicated by a box. Recombination events are indicated by a horizontal black line. Haplotype analyses indicate that LQT3 and SCN5A are tightly linked in all chromosome 3-linked families.
Figure 1C:
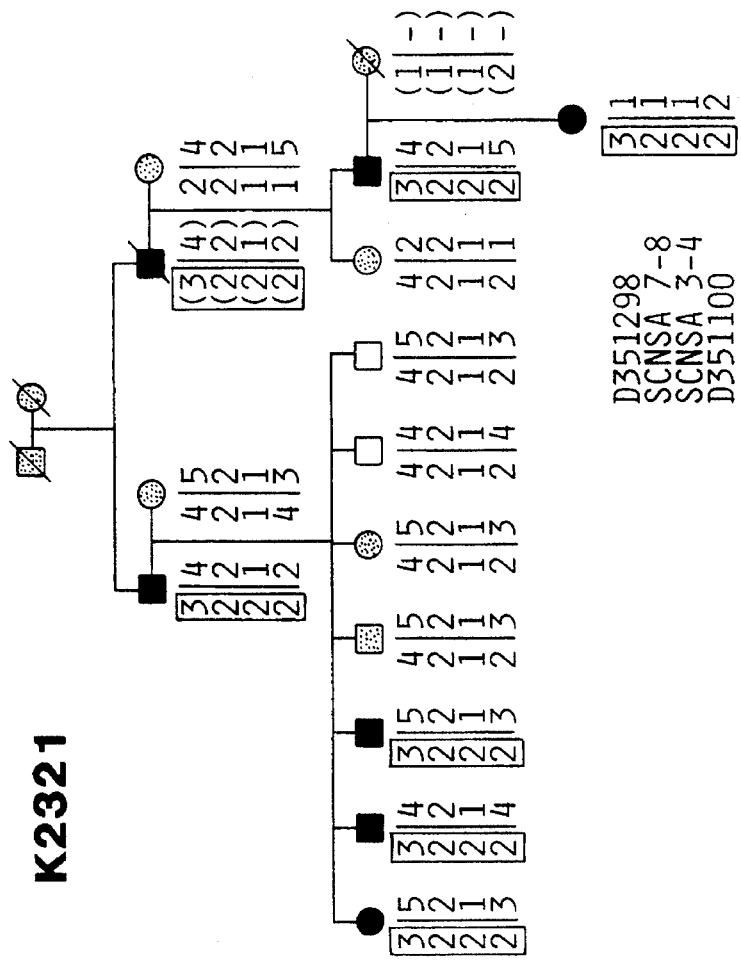
Figure 1B:
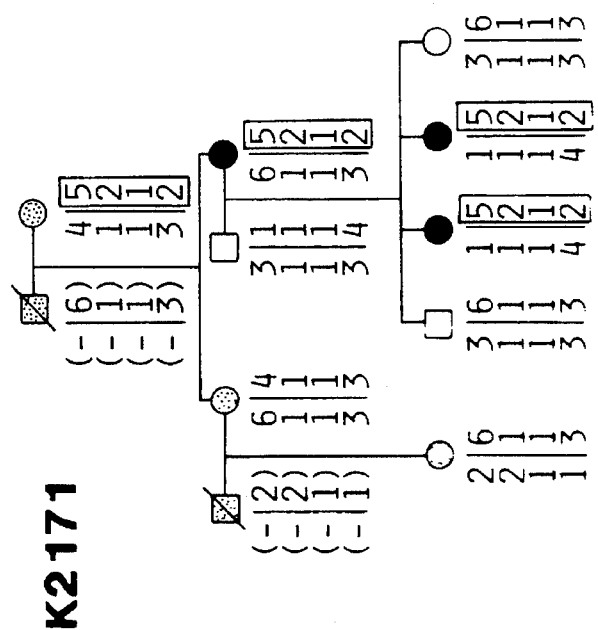

The present invention has used genotypic analyses to show that SCN5A is tightly linked to LQT3 in three unrelated families (details provided in the Examples). The same intragenic deletion of SCN5A appears in affected members of two of these families. Both families are North American of European descent, one German and the other English. Examination of a genealogy database failed to reveal a relationship between these families for more than eight generations. Furthermore, genotypic analyses of these kindreds indicated different haplotypes on the disease chromosome as shown in FIG. 1. Thus it is unlikely these families are related. This deletion is due to a nine base pair deletion resulting in a deletion of three amino acids, $K_{1505}$-$P_{1506}$-$Q_{1507}$ (KPQ) in the cytoplasmic linker between DIII and DIV. These deletions disrupted sequences within a region of known importance for sodium channel inactivation, suggesting a likely cellular mechanism for chromosome 3-linked LQT.

Additional evidence supports a role for SCN5A in the pathogenesis of LQT. Pharmacologic data, for example, suggest that abnormal cardiac sodium channel function could cause LQT. Toxins and drugs that slow the rate of sodium channel inactivation, or shift the voltage-dependence of channel activation or inactivation, can prolong cardiac action potential duration and induce arrhythmias (Honerjager, 1982). Molecular genetic studies also support a link between sodium channel inactivation and clinical electrophysiologic abnormalities. Studies of hyperkalemic periodic paralysis and paramyotonia congenita indicate that missense mutations in the skeletal muscle sodium channel gene (SCN4A) cause myotonia (Fontaine et al., 1990; Ptacek et al., 1991, 1992; Rojas et al., 1991; McClatchey et al., 1992b, 1992c; Ebers et al., 1991; Rudolph et al., 1992; Lerche et al., 1993). Physiologic data show that these mutations affect sodium channel inactivation, leading to repetitive depolarizations, consistent with the myotonic phenotype (Yang et al., 1994). By analogy, similar mutations in the cardiac sodium channel gene could cause a phenotype like LQT.

The mutations in HERG, a putative cardiac potassium channel gene, cause the chromosome 7-linked form of LQT (details provided in Examples). The mutations identified in HERG, and the biophysics of potassium channel alpha subunits, suggest that chromosome 7-linked LQT results from dominant-negative mutations and a resultant reduction in functional channels. In chromosome 3-linked LQT, by contrast, the LQT-associated deletions identified in SCN5A are likely to result in functional cardiac sodium channels with altered properties, such as delayed inactivation or altered voltage-dependence of channel inactivation. Delayed sodium channel inactivation would increase inward sodium current, depolarizing the membrane. This affect is similar to the altered membrane potential expected from HERG mutations where outward potassium current is decreased. It is unlikely that more deleterious mutations of SCN5A would cause LQT. A reduction of the total number of cardiac sodium channels, for example, would be expected to reduce action potential duration, a phenotype opposite that of LQT. The present invention describes mutations which cause the deletion of three amino acids, KPQ, in the cytoplasmic linker between DIII and DIV. The KPQ sequence is highly conserved, suggesting the presence of genetic pressure for its conservation during evolution (FIG. 2). The cytoplasmic peptide segment that links DIII and DIV is the region responsible for fast inactivation (West et al., 1992). Heterologous expression of neural sodium channels in the form of two polypeptides lacking this DIII/DIV linker results in a sodium current with greatly slowed inactivation (Stuhmer et al, 1989). Site-directed mutagenesis studies of this region in SCN4A have focused on another amino acid triplet, $I_{1488}$-$F_{1489}$-$M_{1490}$ (IFM). Mutations of these amino acids to glutamine residues eliminate sodium channel fast inactivation, but leave slow inactivation intact (West et al., 1992). It will be of interest to determine if the KPQ deletion has a similar functional effect on cardiac sodium channel inactivation.

The data predict a likely cellular mechanism for chromosome 3-linked LQT. Delayed myocellular sodium channel inactivation would prolong action potential duration and the QT interval. Excessive prolongation could result in reactivation of L-type calcium or sodium channels, thereby leading to secondary depolarizations, a likely mechanism of torsades de pointes (Antzelevitch and Sicouri, 1994).

No mutation has yet been identified in SCN5A in kindred 2171, the third chromosome 3-linked LQT family. Although the disease phenotype in this kindred appears to be linked to SCN5A, SSCP analyses of sequences encoding the putative inactivation region failed to show a deletion or other anomalies. Presumably, the disease in this family results from SCN5A mutations in another region of this approximately 35 kb gene. Mutational analyses of hyperkalemic periodic paralysis and paramyotonia congenita families have demonstrated several other regions of SCN4A that are important for channel inactivation (Fontaine et al., 1990; Ptacek et al., 1991, 1992; Rojas et al., 1991; McClatchey et al., 1992b, 1992c; Ebers et al., 1991; Rudolph et al., 1992; Lerche et al., 1993).

Although LQT kindreds 2321 and 2322 appear unrelated, both had the same KPQ deletion. The haplotype of the affected chromosome in each family was distinct, but this does not exclude the possibility of a distant relationship. Continued genotypic analysis of sequences near SCN5A may help determine if these deletions arose separately, or in a single progenitor.

Presymptomatic diagnosis of LQT has depended on identification of QT prolongation on electrocardiograms. Unfortunately, electrocardiograms are rarely performed in young, healthy individuals. In addition, many LQT gene carriers have relatively normal QT intervals, and the first sign of disease can be a fatal cardiac arrhythmia (Vincent et al., 1992). Now that two LQT genes have been identified, genetic testing for this disorder can be contemplated. This will require continued mutational analyses and identification of additional LQT genes. With more detailed phenotypic analyses, phenotypic differences between the varied forms of LQT may be discovered. These differences may be useful for diagnosis and treatment.

The identification of the association between the SCN5A and HERG gene mutations and LQT permits the early presymptomatic screening of individuals to identify those at risk for developing LQT. To identify such individuals, the SCN5A and/or HERG alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO) dot blot analysis and PCR-SSCP analysis. For example, either (1) the nucleotide sequence of both the cloned alleles and normal SCN5A gene or appropriate fragment (coding sequence or genomic sequence) are determined and then compared, or (2) the RNA transcripts of the SCN5A gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the SCN5A or HERG gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal SCN5A gene.

Alternatively, polymerase chain reactions (PCRs) are performed with primer pairs for the 5' region or the exons of the SCN5A or HERG gene. PCRs can also be performed with primer pairs based on any sequence of the normal SCN5A or HERG gene. For example, primer pairs for one of the introns can be prepared and utilized. Finally, PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common SCN5A or HERG gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal SCN5A or HERG gene and defective genes. This comparison is performed in steps using small (~500 bp) restriction fragments of the SCN5A or HERG gene as the probe. First, the SCN5A or HERG gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the SCN5A or HERG gene fragments are transcribed in vitro using the SP6 transcription system, well known in the art, in the presence of [α-$^{32}$P]GTP, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the SCN5A or HERG fragment and the SCN5A or HERG allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the SCN5A or HERG gene and the consequent presence of long QT syndrome. These variants can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk for LQT at, or even before, birth. Presymptomatic diagnosis of LQT will enable prevention of these disorders. Existing medical therapies, including beta adrenergic blocking agents, may prevent and delay the onset of problems associated with the disease. Finally, this invention changes our understanding of the cause and treatment of common heart disease like cardiac arrhythmias which account for 11% of all natural deaths. Existing diagnosis has focused on measuring the QT interval from electrocardiograms. This method is not a fully accurate indicator of the presence of long QT syndrome. The present invention is a more accurate indicator of the presence of the disease.

The present invention is further detailed in the following Examples, which are offered by way of illustration and are not intended to limit the invention in any manner. Standard techniques well known in the art or the techniques specifically described below are utilized.

EXAMPLE 1

Methods for Phenotypic Evaluation

For the SCN5A studies, three previously-described LQT kindreds (K2171, K2321 and K2322) were studied (Jiang et al., 1994). For the HERG studies, LQT kindreds were ascertained from medical clinics throughout North America. Phenotypic criteria were identical to those used in previous studies (Keating et al., 1991a; Keating et al., 1991b; Keating, 1992). Individuals were evaluated for LQT based on the QT interval corrected for heart rate (QTc; Bazzett, 1920), and the presence of syncope, seizures, and aborted sudden death. Informed consent was obtained from each individual, or their guardians, in accordance with local institutional review board guidelines. Phenotypic data were interpreted without knowledge of genotype. Symptomatic individuals with a corrected QT interval (QTc) of 0.45 seconds or greater and asymptomatic individuals with a QTc of 0.47 seconds or greater were classified as affected. Asymptomatic individuals with a QTc of 0.41 seconds or less were classified as unaffected. Asymptomatic individuals with QTc between 0.41 and 0.47 seconds and symptomatic individuals with QTc of 0.44 seconds or less were classified as uncertain.

EXAMPLE 2

Linkage Analysis

Pairwise linkage analysis was performed using MLINK in LINKAGE v5.1 (Lathrop et al., 1985). Assumed values of 0.90 for penetrance and 0.001 for LQT gene frequency were used. Gene frequency was assumed to be equal between males and females.

EXAMPLE 3

Isolation of SCN5A Genomic Clones and Partial Characterization of Genomic Structure SCN5A probes were generated using the products of PCR reactions with human genomic DNA and primer pairs based on SCN5A cDNA sequences. One primer pair, 5'ACTTTCATCGTACTGAATAAAGGCAA3' (SEQ ID NO:1) and 5'GAGTGAACCAGAATCTTCACAGC3' (SEQ ID NO:2), was designed from 5' coding sequences and yielded the predicted product of 118 bp.

The second primer pair, 5'GGACCGTGAGTCCATCGTGTGA3' (SEQ ID NO:3) and 5'AGCCCATTCACAACATATACAGTCT3' (SEQ ID NO:4), was derived from the 3' non-coding sequences and yielded a product of 336 bp.

The third primer pair, 5'AGCAACTTCATCCCAGCTGCTGAG3' (SEQ ID NO:5) and 5'CTCCCAGCATCTCAGGTCAAGTG3' (SEQ ID NO:6), was based on 3' non-coding sequences and yielded a product of 297 bp. These PCR products were purified from 2% agarose gels, radiolabeled to high specific activity and used to screen a human genomic P1 library (Sternberg, 1990).

To characterize the genomic structure of SCN5A exons encoding the cytoplasmic linker between DIII–DIV, sequencing primers based on cDNA sequences and predicted genomic structure (McClatchey et al., 1992a; Gellens et al., 1992) were designed. The primer pair for presumed exon 21 (based on the structure of SCN4A) was 5'TATGAAGAGCAGCCTCAGTGGGAA3' (SEQ ID NO:7) and 5'CTTTTTCTTCTGTTGGTTGAAGTTG3' (SEQ ID NO:8). Primers for presumed exon 22 were 5'TTAGGGGGCCAGGACATCTTC3' (SEQ ID NO:9) and 5'CAGGGGCCGTGGGATGGGCTTCTGG3' (SEQ ID NO:10). Primers for presumed exon 23 were 5'CACCATATTCAAGCAGATCAG3' (SEQ ID NO:11) and 5'CTGCGCCACTACTACTTCACC3' (SEQ ID NO:12). These primers were used to determine intronic sequences from SCN5A clones as described (Wang and Keating, 1994).

EXAMPLE 4

Isolation of HERG Genomic and cDNA Clones

HERG probes were generated using the products of PCR reactions with human genomic DNA and primer pairs 1–10, 6–13 and 15–17 (see Table 1). These products were cloned, radiolabeled to high specific activity and used to screen a human genomic P1 library (Sternberg, 1990). Positive clones were purified, characterized and used for FISH and DNA sequence analyses. To isolate HERG cDNA clones, genomic probes containing HERG coding sequences were used to probe $10^6$ recombinants of a human hippocampal cDNA library (Stratagene). A single clone containing ~2.2 kb of HERG coding sequence was isolated and characterized.

EXAMPLE 5

YAC-based Mapping of HERG

A PCR assay specific for the 3' untranslated region of HERG (employing primers 5'GCTGGGCCGCTCCCCT-TGGA3' (SEQ ID NO:13) and 5'GCATCTTCATTAATTAT-TCA3' (SEQ ID NO:14) and yielding a 309-bp product) was used to screen a collection of YAC clones highly enriched for human chromosome 7 (Green et al., in press). Two positive YAC clones were identified (yWSS2193 and yWSS1759), both were contained within a larger contig that includes YACs positive for the genetic marker D7S505 (Green et al., 1994).

EXAMPLE 6

Fluorescent In Situ Hybridization

Metaphase chromosome spreads were prepared from normal cultured lymphocytes (46 X,Y) by standard procedures of colcimid arrest, hypotonic treatment and acetic acid-methanol fixation. HERG P1 clone 16B4 was labeled by incorporation of biotin-14-dATP (BioNick System, Gibco-BRL), hybridized to metaphase spreads and detected with streptavidin-Cy3 according to standard methods (Lichter et al., 1988). To identify chromosome 7, a digoxigenin-labeled centromere-specific α-satellite probe (Oncor) was co-hybridized and detected with antidigoxigenin-FITC. Chromosomes were counterstained with DAPI and visualized directly on the photomicroscope.

EXAMPLE 7

SSCP Analysis

Genomic DNA samples were amplified by PCR and used in SSCP analyses as described (Orita et al., 1989; Ptacek et al., 1991). Primer pairs used for this study are shown in Tables 1 and 2. Annealing temperature was 62° C. (for the SCN5A studies) or 58° C. (for the HERG studies) for all PCR reactions. were diluted with 50 µl of 0.1% SDS/1 mM EDTA and 50 µl of 95% formamide dye. For HERG, reactions (10 µl) were diluted with 40 µl of 0.1% SDS/1 mM EDTA and 30 µl of 95% formamide dye. Diluted products were denatured by heating at 94° C. or 100° C. for 5 or 10 minutes, and 3–5 µl of each sample were separated by electrophoresis on either 7.5% or 10% non-denaturing polyacrylamide gels (50 acrylamide:1 Bis-acrylamide) at 4° C. Electrophoresis was carried out at 40–50 watts for 2 to 5 hours. Gels were transferred to 3 MM filter paper, dried and exposed to X-ray film at −80° C. for 12–36 hours.

TABLE 1

HERG PCR Primers

| Name | Position | Sequence | SEQ ID NO: |
|---|---|---|---|
| 1 L | 1147–1166 | GACGTGCTGCCTGAGTACAA | 21 |
| 2 L | 1291–1312 | TTCCTGCTGAAGGAGACGGAAG | 22 |
| 3 L | 1417–1437 | ACCACCTACGTCAATGCCAAC | 23 |
| 4 L | INTRON I | TGCCCCATCAACGGAATGTGC | 24 |
| 5 L | 1618–1636 | GATCGCTACTCAGAGTACG | 25 |
| 6 L | 1802–1823 | GCCTGGGCGGCCCCTCCATCAA | 26 |
| 7 R | 1446–1426 | CACCTCCTCGTTGGCATTGAC | 27 |
| 8 R | 1527–1503 | GTCGAAGGGGATGGCGGCCACCATG | 28 |
| 9 R | INTRON I | TACACCACCTGCCTCCTTGCTGA | 29 |
| 10 R | 1643–1623 | GCCGCGCCGTACTCTGAGTAG | 30 |
| 11 R | 1758–1736 | CAGCCAGCCGATGCGTGAGTCCA | 31 |
| 12 R | INTRON II | GCCCGCCCCTGGGCACACTCA | 32 |
| 13 R | 2034–2016 | CAGCATCTGTGTGTGGTAG | 33 |
| 14 R | INTRON III | GGCATTTCCAGTCCAGTGC | 34 |
| 15 L | 2259–2278 | CCTGGCCATGAAGTTCAAGA | 35 |
| 16 L | 2214–2233 | GCACTGCAAACCCTTCCGAG | 36 |
| 17 R | 25S0–2529 | GTCGGAGAACTCAGGGTACATG | 37 |

NOTE

All primers are shown in 5' to 3' direction. Sense-strand oligonucleotides are indicated with an "L" and anti-sense oligonucleotides are indicated with an "R". cDNA sequence was obtained from the Genbank database, nucleotide numbering begins with the initiator methionine.

TABLE 2

PCR Primers Used to Define SCN5A Polymorphisms and Mutations

| Primer | Sequence | SEQ ID NO: | Region Amplified | Exon |
|---|---|---|---|---|
| 1 L | GCCTGTCTGATCTCCCTGTGTGA | 38 | DIII/S6; IDIII–IV | 21 |
| 2 R | ACCCAGCCCAGTGGGGAGCTGGT | 39 | | |
| 3 L | CCATGCTGGGGCCTCTAAAACC | 40 | IDIII–IV | 22 |
| 4 R | GGCTCTGATGGCTGGCCATGTG | 41 | | |
| 5 L | CCCAGCGAGCACTTTCCATTTG | 42 | IDIII–IV; DIV/S1–S3 | 23 |
| 6 R | GCTTCTCCGTCCAGCTGACTTGTA | 43 | | |
| 7 L | GAGCCCAGCCGTGGGCATCCT | 44 | DIV/S6 | 24 |
| 8 R | GTCCCCACTCACCATGGGCAG | 45 | | |

NOTE

All primers are shown in 5' to 3' direction. Sense-strand oligonucleotides are indicated with an "L" and anti-sense oligonucleotides are indicated with an "R".

D=domain; ID=interdomain; S=membrane spanning segment.

EXAMPLE 8

Sequence Analysis of SSCP Conformers

Normal and aberrant SSCP conformers were cut directly from dried gels and eluted in 75–100 μl of distilled water at either 37° C. or 65° C. for 30 minutes. Ten μl of the eluted DNA was used as template for a second PCR reaction using the original primer pair. Products were fractionated in 2% low-melting temperature agarose gels (FMC), and DNA fragments were purified and sequenced directly by cycle sequencing (Wang and Keating, 1994). Alternatively, purified PCR products were cloned into pBluescript II SK+ (Stratagene) using the T-vector method as described (Marchuk et al., 1990). Plasmid DNA samples were purified and sequenced by the dideoxy chain termination method using SequiTherm Polymerase (Epicentre Technologies) or as previously described (Curran et al., 1993a).

EXAMPLE 9

Northern Analysis

A multiple tissue Northern blot containing ~2 μg/lane of poly-A+ mRNA was purchased from Clonetech (Human MTN blot 1). A high specific activity (>1.5×10$^9$ cpm/μg DNA), radiolabeled HERG cDNA fragment containing nucleotides 679–2239 of the coding sequence was prepared by random hexamer priming as described (Feinberg and Vogelstein, 1983). Probe was added to the hybridization solution at final concentration of 5×10$^6$ cpm/ml. Hybridization was carried out at 42° C. for 24 hours in 20 ml of Quickhyb solution (Stratagene). Final washes were carried out at 65° C. for 30 minutes in a solution of 0.1% SDS/0.1X SSC.

EXAMPLE 10

Linkage Analysis of SCN5A

To determine the chromosomal location of an LQT gene, linkage analysis was performed. Previously 3 LQT families had been linked to chromosome 3p ((Jiang et al., 1994). In that study two families, K2171 and K2321 showed complete linkage to markers at D3S1100 and D3S1298. The combined pairwise lod scores of the three linked families were 6.72 and 6.39 respectively, at θ=0.001. Haplotype analysis performed in families K2171, K2321 and K2322 had further refined the position of this locus. Obligate recombinants were identified at D3S1211 and D3S1767, defining the telomeric and centromeric flanking markers respectively. The interval between these flanking loci is estimated to be 17.6 centiMorgans (Jiang et al., 1994).

In 1995, SCN5A was mapped to chromosome 3p21 (George et al., 1995). To test the candidacy of SCN5A for LQT, single-stranded conformation polymorphism (SSCP) analyses were used to identify polymorphisms within this gene, and then linkage analyses in chromosome 3-linked families were performed. Since the genomic structure of SCN5A was unknown, oligonucleotide primer pairs were designed from published SCN5A cDNA sequences (Gellens et al., 1992) based on the assumption that the genomic structure of SCN5A would be similar to the known structure of SCN4A, the skeletal muscle sodium channel gene (McClatchey et al., 1992a). To facilitate this work, two genomic P1 clones were identified and partially characterized. These clones spanned the entire SCN5A gene. Primers based on sequences predicted to encode the cytoplasmic region between DIII and DIV were synthesized. This region corresponds to exons 21–23 of SCN4A and is known to be critical for channel inactivation. These primers were used to characterize the flanking introns by cycle sequencing. Additional primers were designed to these intronic sequences for SSCP analyses (Table 2). Primer pairs which gave appropriately sized products from genomic DNA were used to screen DNA samples from patients. An aberrant SSCP conformer was identified using primer pair 7–8 (Table 2). The normal and aberrant bands were cloned and sequenced. The aberrant conformer resulted from a C to T substitution at position 3 of codon 1819 (cDNA nucleotide 5607; Gellens et al., 1992). This substitution did not affect the predicted amino acid sequence of SCN5A. The observed heterozygosity for this polymorphism was <0.50. The SCN5A polymorphism was used for genotypic analyses in chromosome 3-linked families (FIG. 1 ). No recombination events between SCN5A and LQT were identified in any of these families. The maximum combined two-point lod score for all chromosome 3-linked families was 2.74 at a recombination fraction of 0.0 (Table 3).

TABLE 3

Pairwise Lod Scores an Recombination Fractions for Linkage of LQT3 with SCN5A

| Marker | Kindred | Recombination Fraction | | | | | | |
|---|---|---|---|---|---|---|---|---|
| | | 0.001 | 0.01 | 0.05 | 0.10 | 0.20 | 0.30 | 0.40 |
| SCN5A/3–4 | K2171 | 0.00 | 0.00 | 0.00 | 0.00 | 0.00 | 0.00 | 0.00 |
| | K2321 | 1.50 | 1.47 | 1.35 | 1.20 | 0.87 | 0.53 | 0.18 |
| | K2322 | 4.03 | 3.95 | 3.62 | 3.20 | 2.34 | 1.47 | 0.61 |
| | TOTAL | 5.53 | 5.43 | 4.97 | 4.40 | 3.22 | 2.00 | 0.79 |
| | $Z_{max} = 5.54, \theta = 0.0$ | | | | | | | |
| SCN5A/7–8 | K2171 | 0.82 | 0.80 | 0.74 | 0.65 | 0.46 | 0.26 | 0.08 |
| | K2321 | 0.12 | 0.12 | 0.10 | 0.08 | 0.04 | 0.02 | 0.00 |
| | K2322 | 1.80 | 1.78 | 1.66 | 1.48 | 1.05 | 0.60 | 0.20 |
| | TOTAL | 2.74 | 2.70 | 2.50 | 2.20 | 1.55 | 0.87 | 0.28 |
| | $Z_{max} = 2.74, \theta = 0.0$ | | | | | | | |

NOTE

Lod scores were calculated assuming autosomal dominant inheritance with a penetrance of 0.90 for all kindreds, as indicated by segregation analysis of these and other LQT kindreds. Assumed were a disease allele frequency of 0.001 and that female and male recombination frequencies were equal. $Z_{max}$ indicates maximum log score. $\theta$ indicates estimated recombination fraction at $Z_{max}$.

When primer pair 3–4 was used in SSCP analyses, an anomalous conformer was identified in DNA samples from affected members of kindreds 2321 and 2322 (FIG. 1). By contrast, only the normal conformer was seen in DNA samples from unaffected members of these families. The combined two-point lod score for linkage between this anomaly and LQT3 was 5.54 (Table 3). Again, no recombination was observed between SCN5A and LQT3, indicating that these loci are tightly linked.

Figure 3:
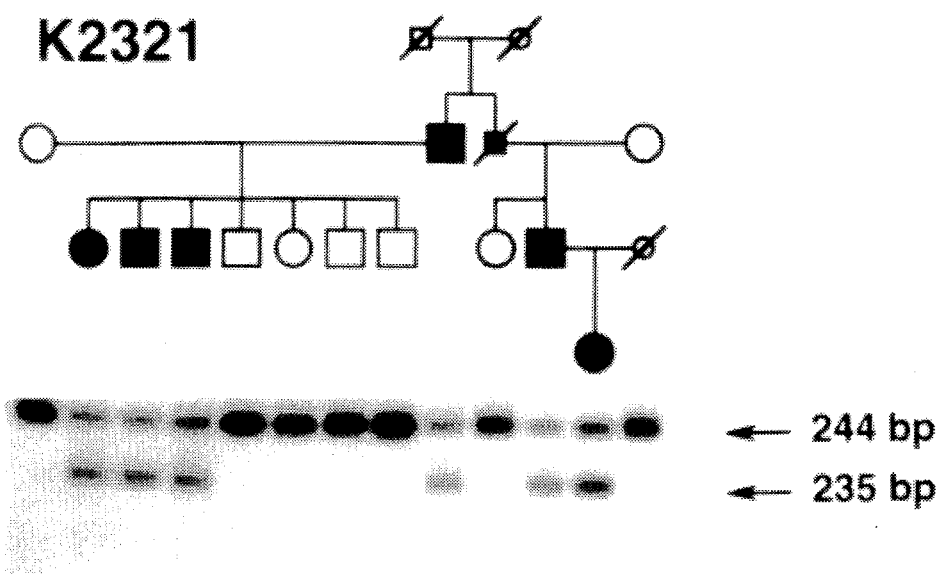
FIG. 3. SCN5A intragenic deletion cosegregates with the disease in kindred 2321. The pedigree structure for kindred 2321 is shown. The results of PCR analyses using primer pair 3–4 and denaturing polyacrylamide gel electrophoresis are shown below each symbol. Note that the 235 bp allele cosegregates with the disease in this family, indicating the presence of a disease-associated intragenic deletion of SCN5A. To avoid phenotypic misclassification, the phenotypic criteria used in this study were stringent, and many individuals were classified as having an uncertain phenotype. Individuals with a QTc of 0.47 seconds or greater were classified as affected, whereas individuals with a QTc of 0.41 seconds or less were considered unaffected. All other individuals were classified as uncertain. If typical criteria were used (individuals with a QTc of 0.44 seconds or greater considered affected and individuals with a QTc less than 0.44 seconds classified as normal), all affected members of kindreds 2321 and 2322 would carry the SCN5A deletion and all unaffected individuals would carry only the normal allele.
Figure 4:
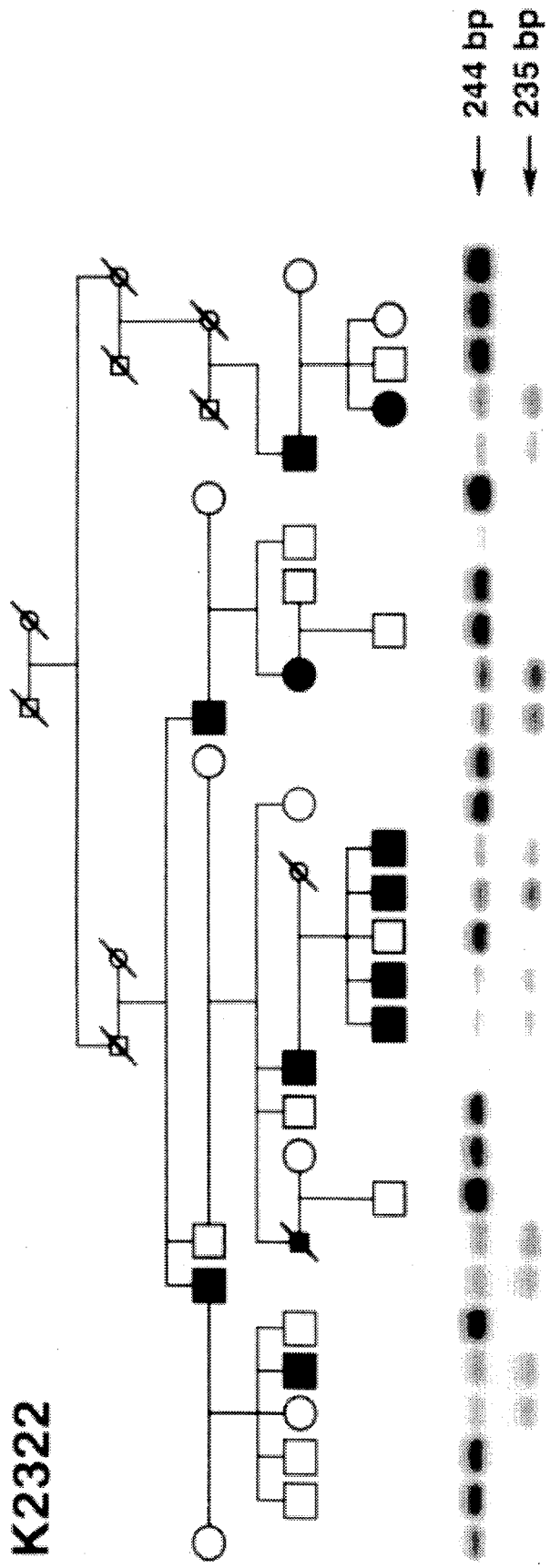
FIG. 4. SCN5A intragenic deletion in kindred 2322. The results of PCR analyses using primer pair 3–4 and denaturing polyacrylamide gel electrophoresis are shown below each symbol. Note that the 235 bp allele cosegregates with the disease in this family, indicating the presence of a disease-associated intragenic deletion. The individuals represented in lanes 4 and 8 carried the deletion but were phenotypically classified as uncertain. These individuals had a QTc of 0.46 seconds, and with less stringent phenotypic criteria would be considered affected.

The mobility shift between the aberrant and normal SSCP conformers identified in kindreds 2321 and 2322 was large, suggesting the possibility of a small deletion. To test this hypothesis, the conformers were separated by electrophoresis on denaturing polyacrylamide gels (FIGS. 3 and 4). These data demonstrated the presence of two products of 235 bp and 244 bp. The 235 bp product was only seen in affected individuals. Furthermore, this aberrant conformer was not observed in more than 500 control individuals. These data indicate the presence of a disease-associated deletion within SCN5A.

Figure 5:
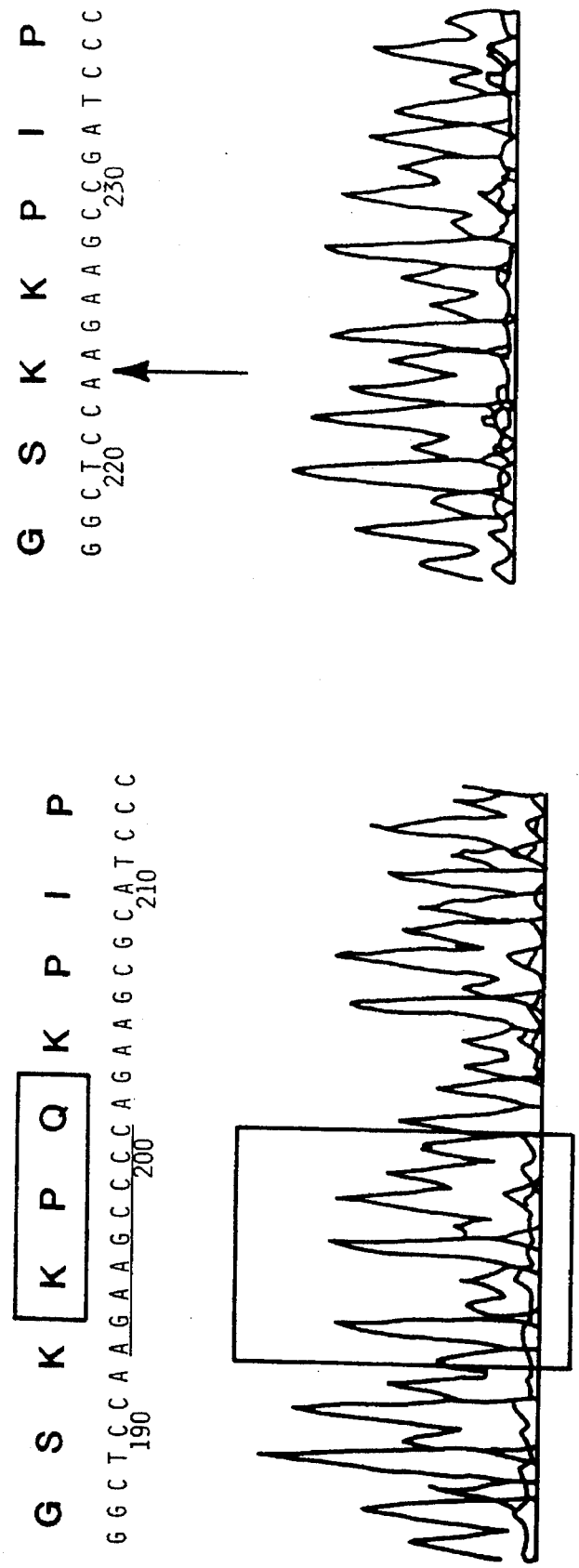
FIGS. 5A and 5B. DNA and amino acid sequence of the SCN5A intragenic deletion associated with LQT. DNA sequence analysis of the SCN5A intragenic deletion identified in kindred 2322. DNA sequence of normal (FIG. 5A) and aberrant (FIG. 5B) PCR products defines a 9 bp deletion. This mutation causes a deletion of 3 amino acids (KPQ) in the cytoplasmic region between DIII and DIV. Deleted sequences are indicated.
Figure 6:
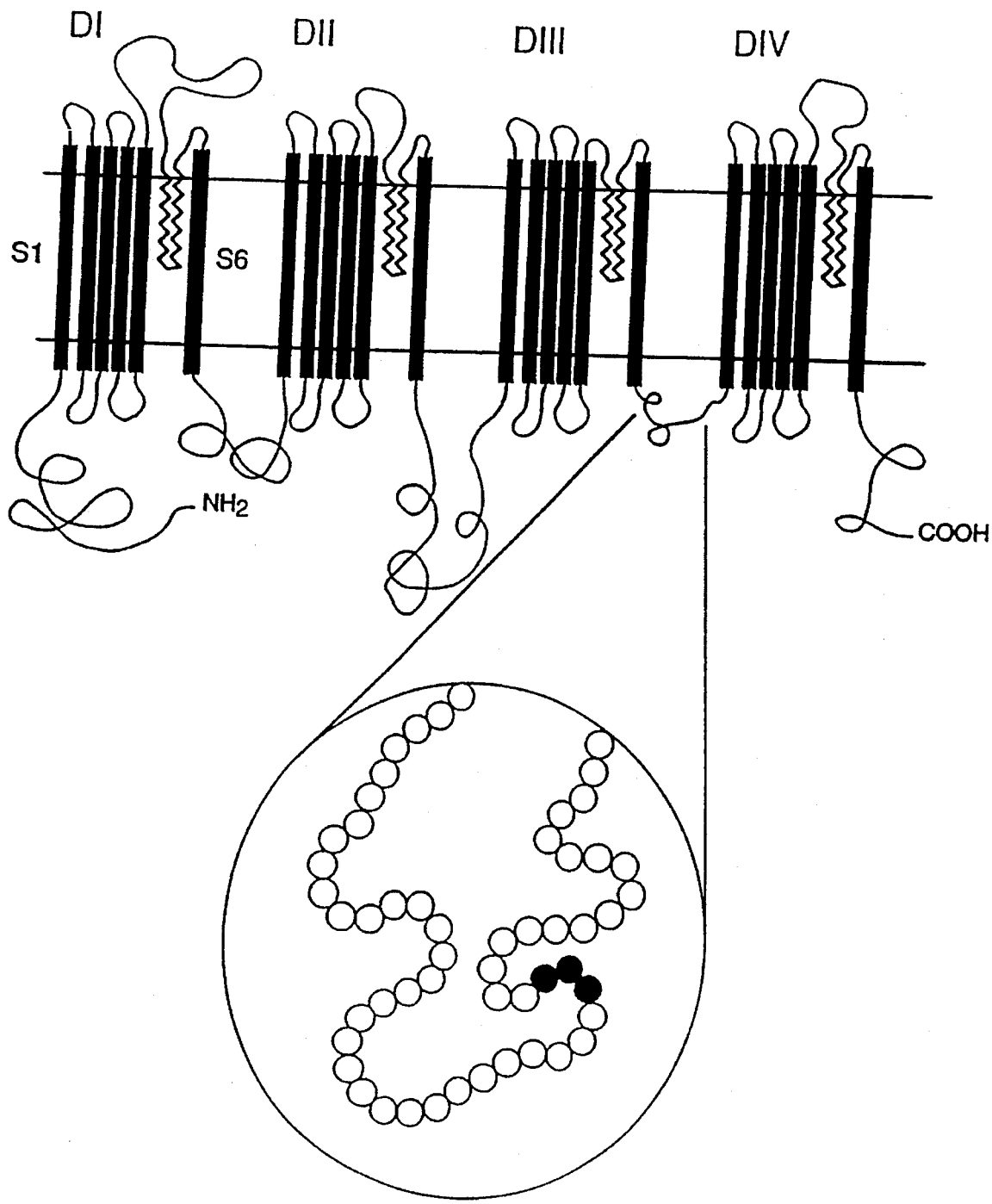
FIG. 6. Schematic representation of the predicted topology of the protein encoded by SCN5A, and the location of the LQT-associated deletion.
Figure 7A:
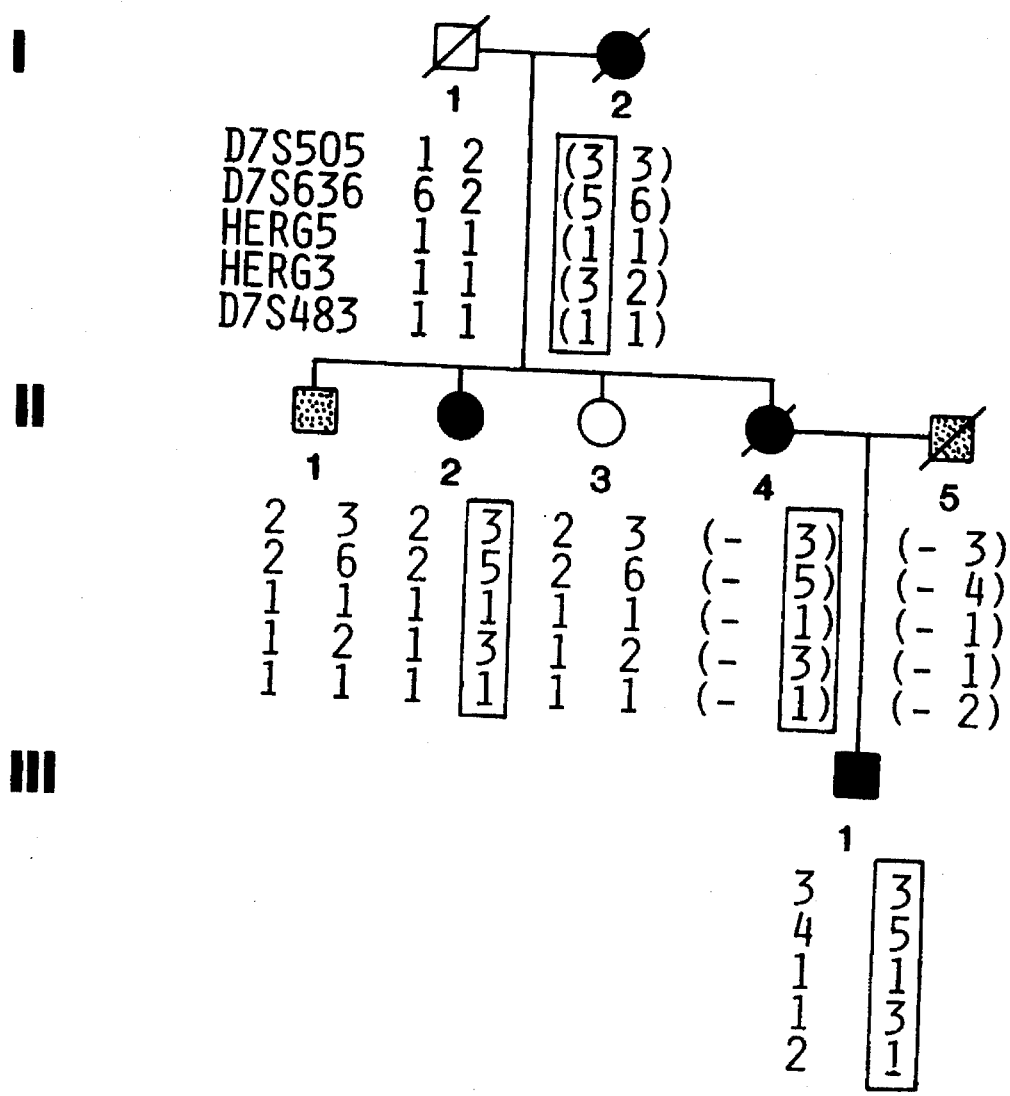
FIGS. 7A–7E. Pedigree structure and genotypic analyses of five new LQT families. Individuals showing the characteristic features of LQT, including prolongation of the QT interval and history of syncope, seizures or aborted sudden death, are indicated by filled circles (females) or squares (males). Unaffected individuals are indicated by empty circles or squares. Individuals with an equivocal phenotype, or for whom phenotypic data are unavailable, are stippled. Circles or squares with a slash denote deceased individuals. Haplotypes for polymorphic markers linked to LQT2 are shown under each individual. These markers include (centromere to telomere) D7S505, D7S636, HERG 5–11, HERG 3–8, D7S483 (Gyapay et al., 1994; Wang et al., submitted). Haplotypes cosegregating with the disease phenotype are indicated by a box. Recombination events are indicated with a horizontal black line. Informed consent was obtained from all individuals, or their guardians, in accordance with local institutional review board guidelines. Haplotype analyses indicate that the LQT phenotype in these kindreds is linked to markers on chromosome 7q35–36.
Figure 7B:
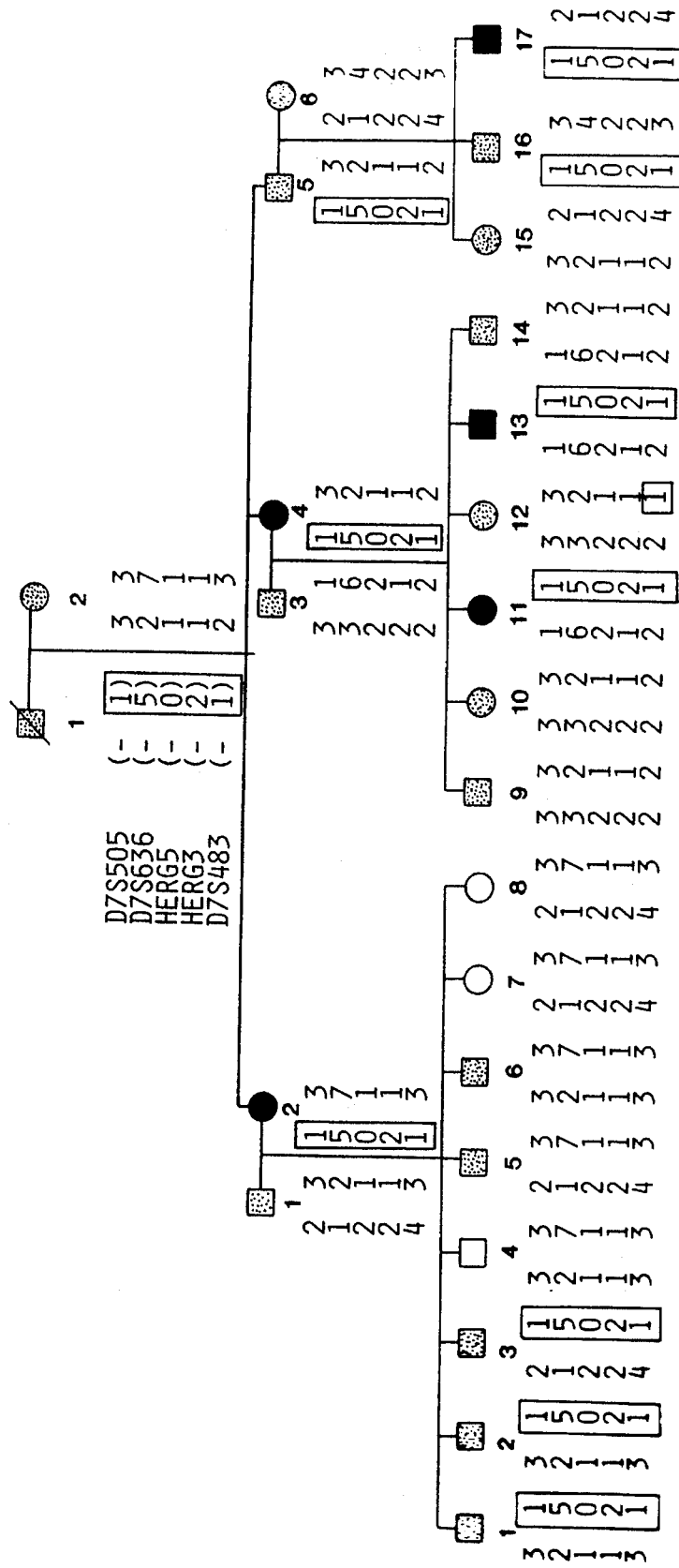
Figure 7C:
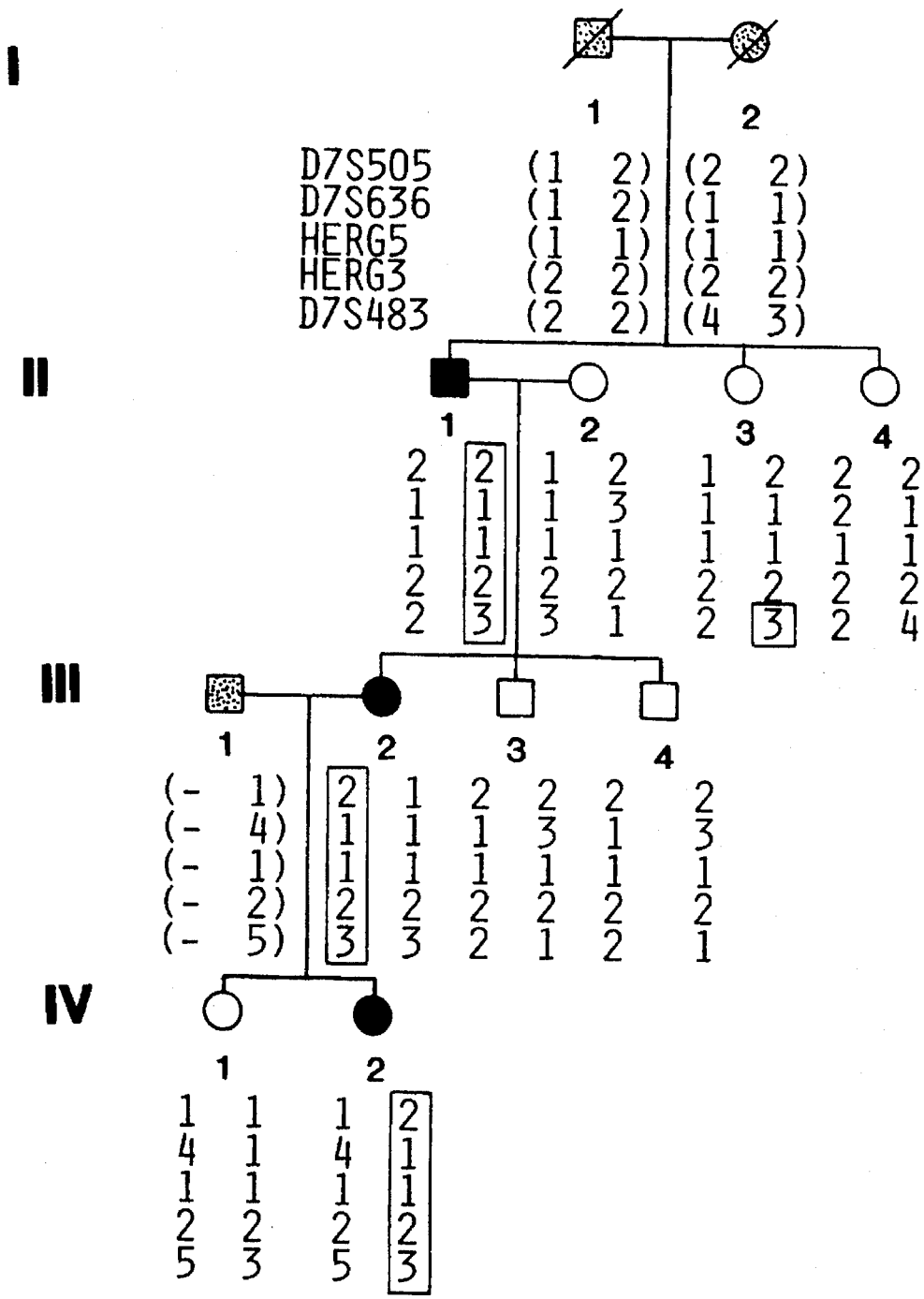
Figure 7D:
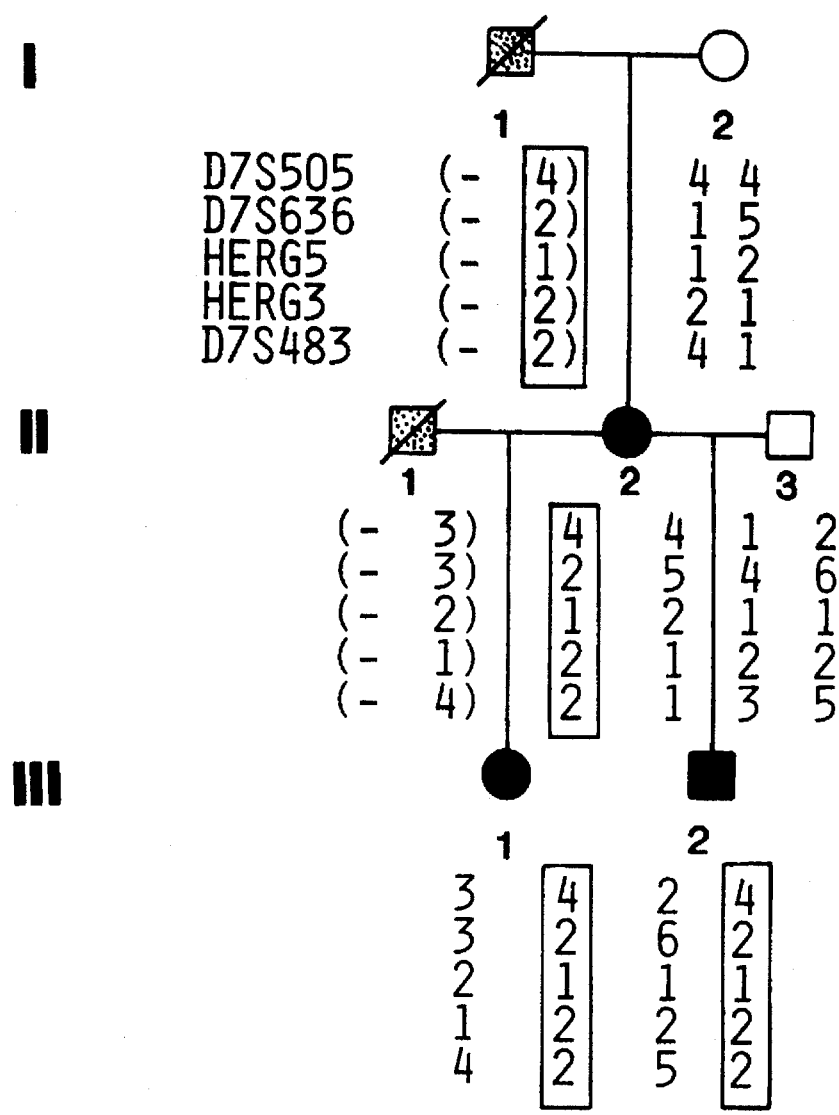
Figure 7E:
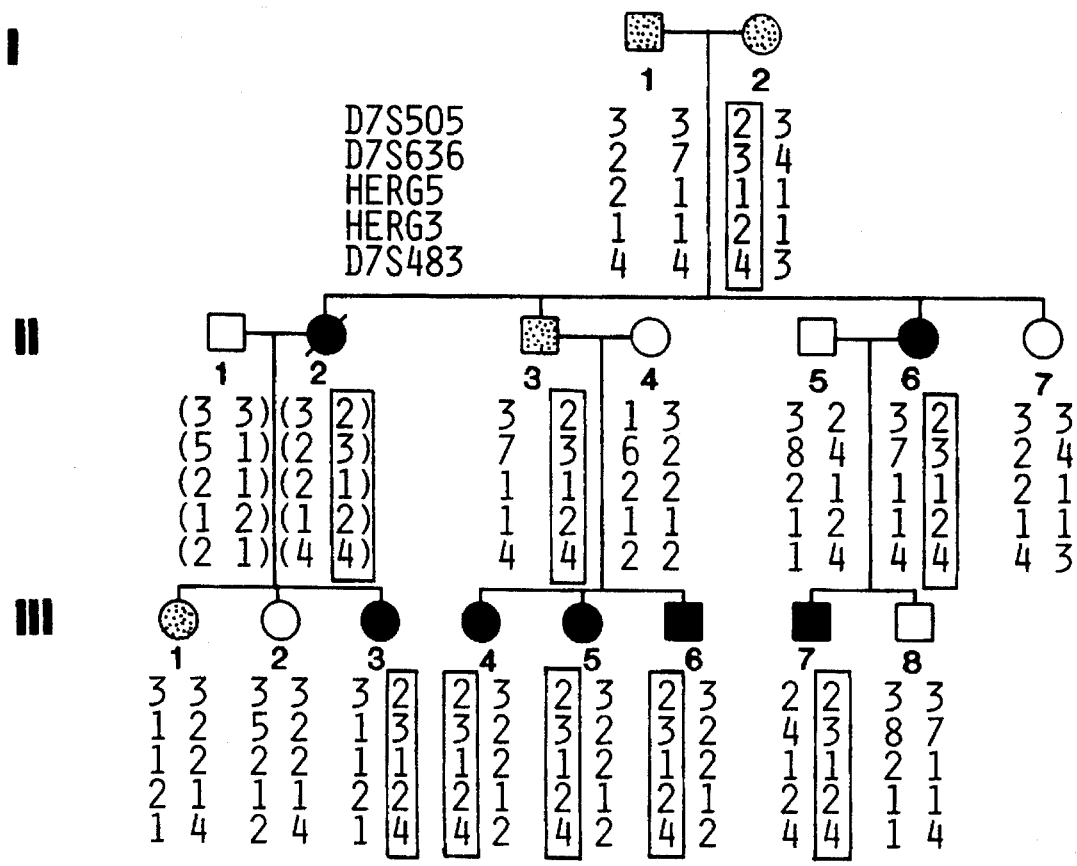

To determine the effect of the LQT-associated deletion on SCN5A structure, the normal and aberrant SSCP conformers were amplified and cycle sequencing was performed. These experiments revealed the presence of a 9 bp deletion beginning at nucleotide 4661 of the cDNA (FIG. 5). The aberrant and normal SSCP conformers were also cloned and sequenced. These experiments confirmed the size and location of the deletion. This deletion disrupts the coding sequence, resulting in a deletion of three conserved amino acids, $K_{1505}$-$P_{1506}$-$Q_{1507}$ (KPQ) in the cytoplasmic linker between DIII and DIV (FIGS. 2 and 6).

DNA sequence analyses of the aberrant conformer in kindred 2321 indicated that the intragenic deletion was identical to that found in kindred 2322. One possible explanation for the identical deletions in these two kindreds is that they are distantly related. Both families were North American of European descent, one German and the other English. Examination of a genealogy database failed to reveal a relationship between these families for more than eight generations. Furthermore, genotypic analyses of these kindreds indicated different haplotypes on the disease chromosome (FIG. 1). The presence of identical deletions in two apparently unrelated LQT families strongly suggests that SCN5A is LQT3.

EXAMPLE 11

Linkage Analysis of HERG

Figure 8:
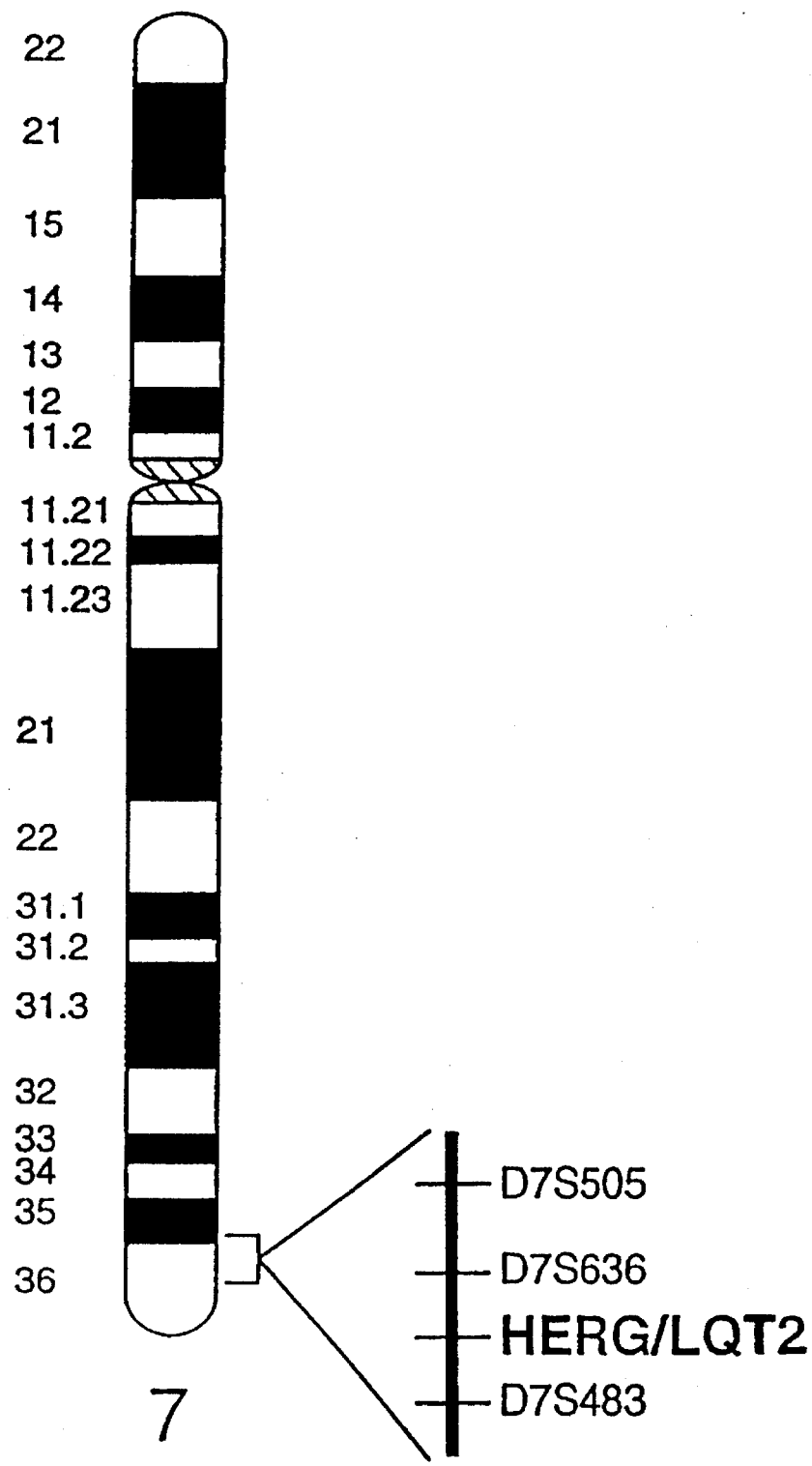
FIG. 8. Idiogram of chromosome 7 showing location of HERG/LQT2.

LQT2 is linked to markers on chromosome 7q35–36. To determine the relative frequency of the three known LQT loci (LQT1, LQT2, LQT3), linkage analyses were performed in families with this disorder. Five LQT families were identified and phenotypically characterized (FIG. 7). These families were unrelated and of varying descent, including Mexican (Spanish), German, English, and Danish. In each case, an autosomal dominant pattern of inheritance was suggested by inspection of the pedigree. Affected individuals were identified by the presence of QT prolongation on electrocardiograms and, in some cases, a history of syncope or aborted sudden death. No patients had signs of congenital neural hearing loss, a finding associated with the rare, autosomal recessive form of LQT, or other phenotypic abnormalities. Genotype analyses with polymorphic markers linked to the known LQT loci suggested that the disease phenotype in these families was linked to polymorphic markers on chromosome 7q35–36 (FIG. 8). The maximum combined two-point lod score for these five families was 5.13 at D7S636 ($\theta=0.0$; Table 4). When combined with a previous study (Jiang et al., 1994; Wang et al., submitted), the maximum combined two-point lod score for the fourteen chromosome 7-linked families was 26.14, also at D7S636 ($\theta=0.0$; Table 4). Haplotype analyses were consistent with previous studies, placing LQT2 between D7S505 and D7S483 (FIG. 8; Wang et al., submitted), localizing this gene to chromosome 7q35–36.

HERG maps to chromosome 7q35–36. HERG was previously mapped to chromosome 7 (Warmke and Ganetzky, 1994). To test the candidacy of this gene, the localization of HERG was refined using two physical mapping techniques. First, HERG was mapped on a set of yeast artificial chromosome (YAC) contigs constructed for chromosome 7 (Green et al., 1994). HERG was localized to the same YAC as D7S505, a polymorphic marker that was tightly linked to LQT2 (Table 4). Second, HERG was mapped to chromosome 7q35–36 using fluorescent in situ hybridization (FISH) with a P1 genomic clone containing HERG.

TABLE 4

Maximum Pairwise Lod Scores and Recombination Fractions for Linkage of LQT2 with HERG, and Polymorphic Markers on Chromosome 7

| Locus | Families From Present Study | | Families Studied To Date | |
|---|---|---|---|---|
| | $Z_{max}$ | θ | $Z_{max}$ | θ |
| D7S505 | 4.40 | 0.0 | 22.91 | 0.009 |
| D7S636 | 5.13 | 0.0 | 26.14 | 0.00 |
| HERG 3-8 | 0.11 | 0.0 | 6.34 | 0.00 |
| HERG 5-11 | 3.55 | 0.0 | 9.64 | 0.00 |
| D7S483 | 2.48 | 0.0 | 22.42 | 0.00 |

NOTE

Markers are shown in chromosomal order (centromere to telomere, Gyapay et al., 1984). The first column (families from present study) indicates combined lod scores for the five families described in this study. The second column (families studied to date) indicates combined log scores from the five families studied here, and nine families from previous study (Jiang et al., 1994). $Z_{max}$ indicates maximum lod score. θ indicates estimated recombination fraction at $Z_{max}$.

Figure 9:
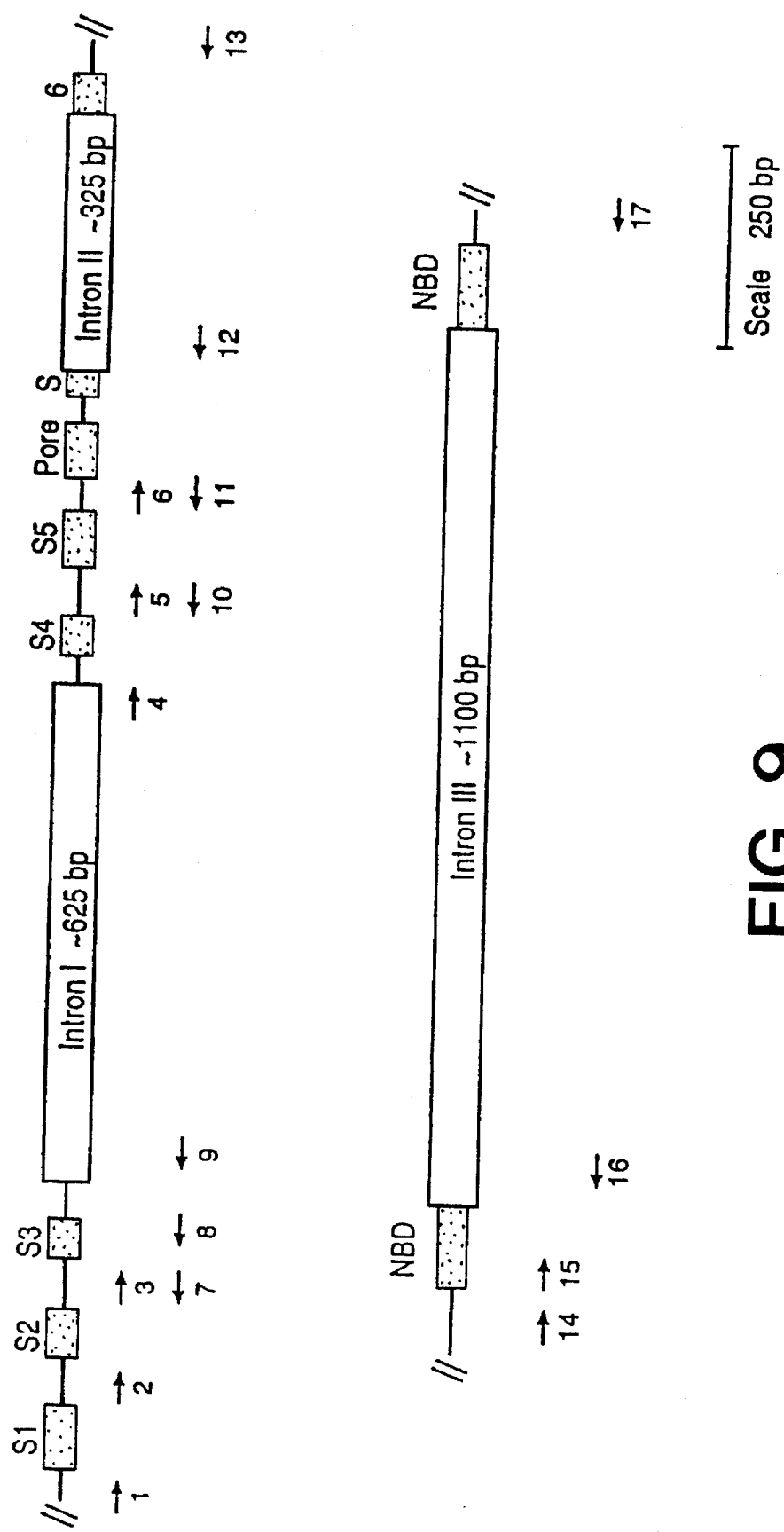
FIG. 9. Partial genomic structure of HERG and location of PCR primers used in this study. Regions encoding predicted membrane spanning domains (S1–S6), the pore domain, and the nucleotide binding domain (NBD) are indicated. The DNA sequence for the intron-exon boundaries are: Intron I, 5'-AGGAGgtgggg(SEQ ID NO: 15) . . . ccccagCTGATC(SEQ ID NO: 16)-3', Intron II, 5'-TGGCTgtgagt(SEQ ID NO: 17) . . . ccccagCCCTC(SEQ ID NO.

To determine if HERG was genetically linked to the LQT locus, SSCP analyses were used to identify polymorphisms within HERG, and linkage analyses were performed in the chromosome 7-linked families. Two aberrant SSCP conformers were identified in DNA samples from patients and controls using primer pairs 5-11, and 3-8 (FIG. 9). These conformers were cloned and sequenced. One abnormal conformer resulted from a C to T substitution at position 3 of codon 489 (cDNA nucleotide 1467, observed heterozygosity=0.37). The second abnormal conformer resulted from an A to G substitution at position 3 of codon 564 (cDNA nucleotide 1692, observed heterozygosity=0.44). Neither substitution affected the predicted amino acid sequence of HERG. HERG polymorphisms were used for genotypic analyses in chromosome 7-linked families (FIG. 7). No recombination events between HERG and LQT were identified in any of these families. The maximum combined lod score for the 14 families was 9.64 (θ=0.0; Table 4). These data indicate that HERG is completely linked to LQT2.

HERG intragenic deletions associated with LQT in two families. To test the hypothesis that HERG is LQT2, SSCP analyses were used to screen for mutations in affected individuals. Since the genomic structure of HERG was unknown, oligonucleotide primer pairs were designed from published (Warmke and Ganetzky, 1994) HERG cDNA sequences (FIG. 9, Table 1). In most cases, single products of expected size were generated. For primer pairs 1-10, 6-13, and 15-17, however, products of greater than expected size were obtained, suggesting the presence of intronic sequences. To examine this possibility, these larger products were cloned and sequenced. DNA sequence analyses identified three introns at positions 1557/1558, 1945/1946, and 2398/2399 of the cDNA sequence (FIG. 9). These boundaries were confirmed by direct DNA sequencing of HERG genomic clones containing HERG (data not shown). To facilitate SSCP analyses, additional primers were designed to intronic sequences.

As indicated previously, SSCP analyses using primer pair 3-8 identified an A to G polymorphism within HERG (cDNA nucleotide 1692). Analysis of kindred 2287 (K2287) using this SSCP polymorphism defined a pattern of genotypes consistent with a null allele (FIG. 7). Possible explanations for these findings included multiple misinheritances, a possibility not supported by previous genotypic analyses, DNA sample errors, base-pair substitutions, or a deletion. To test the hypothesis that the genotypic data were due to a small deletion, PCR analyses of K2287 were repeated using a new primer pair (3-9) flanking the previous set of primers. These experiments identified two products of 170 bp and 143 bp in affected members of K2287 (FIGS. 10A and 10B). By contrast, only a single product of 170 bp was observed in unaffected members of this kindred. Furthermore, only the 170 bp band was seen in DNA samples from more than 200 unaffected individuals. The 143 bp and 170 bp products were cloned from affected individual II-2. Direct sequence analyses of the aberrant PCR product revealed the presence of a 27 bp deletion beginning at position 1498 (ΔI500-F508). This deletion disrupts the third membrane spanning domain (S3) of HERG.

To further test the hypothesis that HERG is LQT2, more SSCP analyses were performed in additional kindreds. SSCP using the primer pair 1-9 identified an aberrant conformer in affected individuals of K2595 (FIG. 11A). Analyses of more than 200 unaffected individuals failed to show this anomaly. The normal and aberrant conformers were cloned and sequenced, revealing a single base deletion at position 1261 (Δ1261). This deletion results in a frameshift in sequences encoding the first membrane spanning domain (S1), leading to a new stop codon within 12 amino acids (FIG. 11B). The identification of intragenic deletions of HERG in two LQT families suggests that HERG mutations can cause LQT.

Three HERG point mutations associated with LQT. To identify additional HERG mutations in LQT2, further SSCP analyses were performed in linked kindreds and sporadic cases. Three aberrant SSCP conformers were identified in affected members of K1956, K2596 and K2015 (FIG. 12A). In each case, the normal and aberrant conformers were cloned and sequenced. In K1956, a C to T substitution at position 1682 was identified. This mutation results in substitution of valine for a highly conserved alanine at codon 561 (A561V), altering the fifth membrane spanning domain (S5) of the HERG protein (FIG. 12B). In K2596, an A to G substitution was identified at position 1408. This mutation results in substitution of aspartic acid for a conserved asparagine at codon 470 (N470D), located in the second membrane spanning domain (S2; FIG. 12B). In K2015, a G to C substitution was identified. This substitution disrupts the splice-donor sequence of intron III, affecting the cyclic nucleotide binding domain (FIG. 12B). None of the aberrant conformers was identified in DNA samples from more than 200 unaffected individuals.

De novo mutation of HERG in a sporadic case of LQT. To substantiate that HERG mutations cause LQT, SSCP was used to screen for mutations in sporadic cases. Primer pair 4-12 identified an aberrant conformer in affected individual II-1 of K2269 (FIG. 13A). This conformer was not identified in either parent or in more than 200 unaffected individuals. Direct DNA sequencing of the aberrant conformer identified a G to A substitution at position 1882. This mutation results in substitution of serine for a highly conserved glycine at codon 628 (G628S) (FIG. 13B), altering the pore forming domain. Genotype analysis of this kindred using nine informative STR polymorphisms confirmed maternity and paternity. The identification of a de novo mutation in a sporadic case demonstrates that HERG is LQT2.

HERG is expressed in the heart. HERG was originally identified from a hippocampal cDNA library (Warmke and Ganetzky, 1994). To determine the tissue distribution of HERG mRNA, partial cDNA clones were isolated and used in Northern analyses. Northern analyses showed strongest hybridization to heart mRNAs, with faint signals in brain, liver, and pancreas (FIG. 14). Non-specific hybridization was also seen in lung, possibly due to genomic DNA contamination. The size of the bands observed in cardiac mRNA was consistent with the predicted size of HERG. Two bands, of ~4.1 and 4.4 kb were identified, possibly due to alternative splicing or the presence of a second related mRNA. These data indicate that HERG is strongly expressed in the heart, consistent with its involvement in LQT.

Mutations in HERG are one cause of LQT. It can be concluded that mutations in HERG cause the chromosome 7-linked form of LQT. Several lines of evidence support this conclusion. First, linkage analyses were used to map an LQT locus (LQT2) to chromosome 7q35–36 in 14 families. Second, physical and genetic mapping were used to place HERG in the same chromosomal region as LQT2. Third, it was demonstrated that HERG is expressed in the heart. Fourth, intragenic deletions of HERG associated with LQT in two families were identified. Fifth, four HERG point mutations in LQT patients were identified. Finally, one of the point mutations arose de novo and occurs within a highly conserved region encoding the potassium-selective pore domain.

The data suggest a likely molecular mechanism for chromosome 7-linked LQT. Although the function of HERG is not yet known, analyses of its predicted amino acid sequence indicates that it encodes a potassium channel α-subunit. Potassium channels are formed from four α-subunits (MacKinnon, 1991), either as homo- or hetero-tetramers (Covarrubias et al, 1991). These biophysical observations suggest that combination of normal and mutant HERG α-subunits could form abnormal HERG channels. This raises the possibility that HERG mutations have a dominant-negative affect on potassium channel function.

The mutations that were identified are consistent with a dominant-negative mechanism (FIG. 15). Two mutations result in premature stop codons and truncated proteins (Δ1261 and the splice-donor mutation). In the first case, only the amino terminus and a portion of the first membrane spanning domain (S1) remain. In the second, the carboxyl end of the protein is truncated, leaving all membrane spanning domains intact. HERG contains a cyclic nucleotide binding domain near the carboxyl terminus, and in both mutations this domain is deleted. In another mutation, an inframe deletion of nine amino acids disrupts the third membrane spanning domain (ΔI500–F508). Two missense mutations also affect membrane spanning domains, A561V in the S5 domain and N470D in S2. Both mutations affect amino acids conserved in the eag family of potassium channels and likely alter the protein's secondary structure. The de novo missense mutation, G628S, occurs in the pore-forming domain. This domain is highly conserved in all potassium channel subunits. This mutation affects a conserved amino acid that is of known importance for ion selectivity. When this substitution was introduced into Shaker H4, potassium ion selectivity was lost (Heginbotham et al., 1994). As discussed above, these mutations could induce the loss of HERG function.

The data have implications for the mechanism of arrhythmias in LQT. Two hypotheses for LQT have previously been proposed (Schwartz et al., 1994). One suggests that a predominance of left autonomic innervation causes abnormal cardiac repolarization and arrhythmias. This hypothesis is supported by the finding that arrhythmias can be induced in dogs by removal of the right stellate ganglion. In addition, anecdotal evidence suggests that some LQT patients are effectively treated by β-adrenergic blocking agents and by left stellate ganglionectomy (Schwartz et al., 1994). The second hypothesis for LQT-related arrhythmias suggests that mutations in cardiac-specific ion channel genes, or genes that modulate cardiac ion channels, cause delayed myocellular repolarization. Delayed myocellular repolarization could promote reactivation of L-type calcium channels, resulting in secondary depolarizations (January and Riddle, 1989). These secondary depolarizations are the likely cellular mechanism of torsade de pointes arrhythmias (Surawicz, 1989). This hypothesis is supported by the observation that pharmacologic block of potassium channels can induce QT prolongation and repolarization-related arrhythmias in humans and animal models (Antzelevitch and Sicouri, 1994). The discovery that one form of LQT results from mutations in a cardiac potassium channel gene supports the myocellular hypothesis.

The presence of a cyclic nucleotide binding domain in HERG suggests a mechanism for the link between altered autonomic nervous activity and arrhythmias in LQT. β-adrenergic receptor activation increases intracellular cAMP and enhances L-type $Ca^{2+}$ channel function. Cyclic AMP may also activate HERG, thereby increasing net outward current and accelerating the rate of myocellular repolarization. Dominant-negative mutations of HERG might interrupt the normal modulation of HERG function by cAMP, thereby permitting a predominant effect on L-type $Ca^{2+}$ channel function. The resulting imbalance would increase the likelihood that enhanced sympathetic tone could induce $Ca^{2+}$ channel-dependent secondary depolarizations, the probable cellular mechanism of torsades de pointes. β-adrenergic blocking agents could act by interrupting the effect of cAMP on L-type $Ca^{2+}$ channels, possibly explaining the beneficial effects of β-blockers in some LQT patients.

The relative frequency of the three LQT loci is not yet known. In this study, five new families with autosomal dominant LQT were identified, and all were linked to chromosome 7. This brings the total number of chromosome 7-linked families to 14. To date, seven families have been linked to chromosome 11 (LQT1), 14 families to chromosome 7 (LQT2), three families to chromosome 3 (LQT3) and three families remain unlinked (Keating et al., 1991a,b; Jiang et al., 1994). Although preliminary, these data suggest that LQT2 is a common form of inherited LQT.

This work may have important clinical implications. Recently, presymptomatic diagnosis has been possible in large families using linkage analysis. Most cases of LQT are sporadic and therefore genetic testing using linkage analysis is not feasible. Continued mutational analyses of LQT2 and LQT3 will facilitate genetic testing for these forms of LQT. Identification and characterization of genes responsible for other forms of LQT will be necessary for the development of generalized diagnostic tests. Improved diagnostic capacity may enable rational therapy. For example, chromosome 7-linked LQT patients may respond to potassium channel activators, like pinacidil.

EXAMPLE 12

Generation of Polyclonal Antibody against SCN5A or HERG

Segments of SCN5A or HERG coding sequence are expressed as fusion protein in *E. coli*. The overexpressed protein is purified by gel elution and used to immunize rabbits and mice using a procedure similar to the one described by Harlow and Lane, 1988. This procedure has been shown to generate Abs against various other proteins (for example, see Kraemer, et al., 1993).

Briefly, a stretch of SCN5A or HERG coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. Identification of the protein as the SCN5A or HERG fusion product is verified by protein sequencing at the N-terminus. Next, the purified protein is used as immunogen in rabbits. Rabbits are immunized with 100 µg of the protein in complete Freund's adjuvant and boosted twice in 3 week intervals, first with 100 µg of immunogen in incomplete Freund's adjuvant followed by 100 µg of immunogen in PBS. Antibody containing serum is collected two weeks thereafter.

This procedure is repeated to generate antibodies against the mutant forms of the SCN5A or HERG gene. These antibodies, in conjunction with antibodies to wild type SCN5A or HERG, are used to detect the presence and the relative level of the mutant forms in various tissues and biological fluids.

EXAMPLE 13

Generation of Monoclonal Antibodies Specific for SCN5A or HERG

Monoclonal antibodies are generated according to the following protocol. Mice are immunized with immunogen comprising intact SCN5A or HERG or SCN5A or HERG peptides (wild type or mutant) conjugated to keyhole limpet hemocyanin using glutaraldehyde or EDC as is well known.

The immunogen is mixed with an adjuvant. Each mouse receives four injections of 10 to 100 µg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow, et al. 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow, et al., 1988. Cells are plated at a density of $2\times10^5$ cells/well in 96 well tissue culture plates. Individual wells are examined for growth and the supernatants of wells with growth are tested for the presence of SCN5A or HERG specific antibodies by ELISA or RIA using wild type or mutant SCN5A or HERG target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

EXAMPLE 14

Sandwich Assay for SCN5A or HERG

Monoclonal antibody is attached to a solid surface such as a plate, tube, bead, or particle. Preferably, the antibody is attached to the well surface of a 96-well ELISA plate. 100 µl sample (e.g., serum, urine, tissue cytosol) containing the SCN5A or HERG peptide/protein (wild-type or routants) is added to the solid phase antibody. The sample is incubated for 2 hrs at room temperature. Next the sample fluid is decanted, and the solid phase is washed with buffer to remove unbound material. 100 µl of a second monoclonal antibody (to a different determinant on the SCN5A or HERG peptide/protein) is added to the solid phase. This antibody is labeled with a detector molecule (e.g., 125-I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of SCN5A or HERG peptide/protein present in the sample, is quantitated. Separate assays are performed using monoclonal antibodies which are specific for the wild-type SCN5A or HERG as well as monoclonal antibodies specific for each of the mutations identified in SCN5A or HERG.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Anderson, et al. (1980). Proc. Natl. Acad. Sci. USA 77, 5399–5403.

Antzelevitch, C. and Sicouri, S. (1994). Clinical relevance of cardiac arrhythmias generated by afterdepolarizations: Role of M cells in the generation of U waves, triggered activity and torsade de pointes. J. Am. Col. Card. 23, 259–277.

Attwell, D., Cohen, I., Eisner, D., Ohba, M., and Ojeda, C. (1979). Steady-state TTX-sensitive ("window") current in cardiac Purkinje fibres. Pflugers Arch. 379, 137–142.

Ausubel, F. M., et al. (1992). Current Protocols in Molecular Biology, (J. Wiley and Sons, N.Y.)

Bazett, H. C. (1920). An analysis of the time-relationships of electrocardiograms. Heart 7, 353–370.

Beaucage & Carruthers (1981). Tetra. Letts. 22, 1859–1862.

Benhorin, J., Kalman, Y. M., Madina, A., Towbin, J., Rave-Harel, N., Dyer, T. D., Blangero, J., et al. (1993). Evidence of genetic heterogeneity in the long QT syndrome, Science 260, 1960–1962.

Berkner, et al. (1988). BioTechniques 6, 616–629.

Berkner (1992). Curr. Top. Microbiol. Immunol. 158, 39–61.

Bonner, T. I., Buckley, N. J., Young, A. C., and Brann, M. R. (1987). Identification of a family of muscarinic acetylcholine receptor genes. Science 237, 527–532.

Brandyopadhyay and Temin (1984). Mol. Cell. Biol. 4, 749–754.

Breakfield and Geller (1987). Mol. Neurobiol. 1, 337–371.

Brinster, et al. (1981). Cell 27, 223–231.

Bruggeman, A., Pardo, L. A., Struhmer, W., and Pongs, O. (1993). Ether-a-go-go encodes a voltage-gated channel permeable to $K^+$ and $Ca^{2+}$ and modulated by cAMP. Nature 365, 445–448.

Buchschacher and Panganiban (1992). J. Virol. 66, 2731–2739.

Capecchi, M. R. (1989). Science 244, 1288.

Cariello (1988). Human Genetics 42, 726.

LIST OF REFERENCES (Cont'd)

Chin, H., Kozak, C., Kim, H-L., Mock, B., and McBride, O. W. (1991). A brain L-type calcium channel α1 subunit gene (CCHL1A2) maps to mouse chromosome 14 and human chromosome 3. Genomics 11, 914–919.

Conner, B. J., et al. (1983). Proc. Natl. Acad. Sci. USA 80, 278–282.
Constantini and Lacy (1981). Nature 294, 92–94.
Cotten, et al. (1990). Proc. Natl. Acad. Sci. USA 87, 4033–4037.
Cotton, et al. (1988). Proc. Natl. Acad. Sci. USA 85, 4397.
Covarrubias, M., Wei, A., and Salkoff, L. (1991). Shaker, shal, shab, and shaw express independent $K^+$ current systems. Neuron 7, 763–773.
Curiel, et al. (1991a). Hum. Gene Ther. 3, 147–154.
Curiel, et al. (1991b). Proc. Natl. Acad. Sci. USA 88, 8850–8854.
Curran, M. E., Atkinson, D. L., Ewart, A. K., Morris, C. A., Leppert, M. F., and Keating, M. T. (1993a). The elastin gene is disrupted by a translocation associated with supravalvular aortic stenosis. Cell 73, 159–168.
Curran, M. E., Atkinson, D., Timothy, K., Vincent, G. M., Moss, A. J., Leppert, M., and Keating, M. T. (1993b). Locus heterogeneity of autosomal dominant long QT syndrome. J. Clin. Invest. 92, 799–803.
Donehower, L. A., et al. (1992). Nature 356, 215.
Ebers, G. C., George, A. L., Barchi, R. L., Ting-Passador, S. S., Kallen, R. G., Lathrop, G. M., Beckman, J. S., Hahn, A. F., Brown, W. F., Campbell, R. D., and Hudson, A. J. (1991). Paramyotonia congenita and hyperkalemic periodic paralysis are linked to the adult muscle sodium channel gene. Ann. Neurol. 30, 810–816.
*Enhancers and Eukaryotic Gene Expression,* Cold Spring Harbor Press, Cold Spring Harbor, N.Y. (1983).
Feinberg, A. P. and Vogelstein, B. A. (1983). Techniques for radiolabeling DNA to high specific activity. Anal. Biochem. 132, 6–13.
Felgner, et al. (1987). Proc. Natl. Acad. Sci. USA 84, 7413–7417.
Fiers, et al. (1978). Nature 273, 113.
Fink, et al. (1992). Hum. Gene Ther. 3, 11–19.

LIST OF REFERENCES (Cont'd)

Finkelstein, J., et al. (1990). Genomics 7, 167–172.
Fontaine, B., Khurana, T. S., Hoffman, E. P., Bruns, G., Haines, J. L., Trofatter, J. A., Hanson, M. P., Rich, J., McFarlane, H., Yasek, D. M., Romano, D., Gusella, J., and Brown, R. (1990). Hyperkalemic periodic paralysis and the adult skeletal muscle sodium channel gene. Science 250, 1000–1002.
Freese, et al. (1990). Biochem. Pharmacol. 40, 2189–2199.
Friedman, T. (1991). In Therapy for Genetic Diseases, T. Friedman, ed., Oxford University Press, pp. 105–121.
Gellens, M., George, A., Chen, L., Chahine, M., Horn, R., Barchi, R., Kallen, R. (1992). Primary structure and functional expression of the human cardiac tetrodotoxin-insensitive voltage-dependent sodium channel. Proc. Natl. Acad. Sci. USA 89, 554–558.
George, A. L., Varkony, T. A., Drabkin, H. A., Han, J., Knops, J. F., Finley, W. H., Brown, G. B., Ward, D. C., and Hass, M. (1995). Assignment of the human heart tetrodotoxin-resistant voltage-gated $Na^+$ channel α-subunit gene (SCN5A) to band 3p21. Cytogenet. Cell. Genet. 68, 67–70.
Gordon, et al. (1980). Proc. Natl. Acad. Sci. USA 77, 7380–7384.
Gorziglia and Kapikian (1992). J. Virol. 66, 4407–4412.
Graham and van der Eb (1973). Virology 52, 456–467.
Green, E. D., Idol, J. R., Mohr-Tidwell, R. M., Branden, V. V., Peluso, D. C., Fulton, R. S., Massa, H. F., Magness, C. L., Wilson, A. M., Kimura, J., Weissenbach, J., and Trask, B. J. (1994). Integration of physical, genetic and cytogenetic maps of human chromosome 7: isolation and analysis of yeast artificial chromosomes for 117 mapped genetic markers. Hum. Mol. Genet. 3, 489–501.
Green, E. D., Branden, V. V., Fulton, R. S., Lira, R., Ueltzen, M. S., Peluso, D. C., Mohr-Tidwell, R. M., Idol, J. R., Smith, L. M., Chumakov, I., LePaslier, D., Cohen, D., Featherstone, T., and Green, P. A human chromosome 7 yeast artificial chromosome (YAC) resource: construction, characterization, and screening. Genomics, in press.
Grompe, M., 1993. Nature Genetics 5, 111–117.
Grompe, M., et al., 1989. Proc. Natl. Acad. Sci. USA 86, 5855–5892.

LIST OF REFERENCES (Cont'd)

Gyapay, G., Morissette, J., Vignal, A., Dib, C., Fizames, C., Millasseau, P., Marc, S., Bernardi, G., Lathrop, M., and Weissenbach, J. (1994). The 1993–94 Genethon human genetic linkage map. Nat. Genet. 7, 246–339.
Harlow & Lane (1988). Antibodies: A Laboratory Manual (Cold Spring Harbor Laboratory, Cold Spring Harbor, N.Y.).
Hasty, P., K., et al. (1991). Nature 350, 243.
Heginbotham, L., Lu, Z., Abramson, T., and MacKinnon, R. (1994). Mutations in the $K^+$ channel signature sequence. Biophys. J. 66, 1061–1067
Helseth, et al. (1990). J. Virol. 64, 2416–2420.
Honerjager, P. (1982). Cardioactive substances that prolong the open state of sodium channels. Rev. Physiol. Biochem. Pharmacol. 92, 1–74.
Inmis et al. (1990). PCR Protocols: A Guide to Methods and Applications, (Academic Press, San Diego, Calif.).
Jablonski, E., et al. (1986). Nuc. Acids Res. 14, 6115–6128.
Jakoby, W. B. and Pastan, I. H. (eds.) (1979). Cell Culture. Methods in Enzymology, volume 58 (Academic Press, Inc., Harcourt Brace Jovanovich (New York)).
January, C. T. and Riddle, J. M. (1989). Early afterdepolarizations: Mechanism of induction and block. Circ. Res. 64, 977–990.
Jervell, A. and Lange-Nielson, F. (1957). Congenital deaf routism, functional heart disease with prolongation of the QT interval, and sudden death. Am. Heart J. 54, 59–78.
Jiang, C., Atkinson, D., Towbin, J. A., Splawski, I., Lehmann, M. H., Li, H., Timothy, K., Taggart, R. T., Schwartz, P. J., Vincent, G. M., Moss, A. J., and Keating M. T. (1994). Two long QT syndrome loci map to chromosomes 3 and 7 with evidence for further heterogeneity. Nat. Genet. 8, 141–147.
Johnson, et al. (1992). J. Virol. 66, 2952–2965.
Kaneda, et al. (1989). J. Biol. Chem. 264, 12126–12129.
Kanehisa (1984). Nucl. Acids Res. 12, 203–213.
Kannel, W. B., Cuppies, A., and D'Agostino, R. B. (1987). Sudden death risk in overt coronary heart diseases: The Framingham study. Am. Heart J. 113, 799–804.

LIST OF REFERENCES (Cont'd)

Keating, M. T., Atkinson, D., Dunn, C., Timothy, K., Vincent, G. M., and Leppert, M. (1991a). Linkage of a cardiac arrhythmia, the long QT syndrome, and the Harvey ras-1 gene. Science 252, 704–706.
Keating, M. T., Atkinson, D., Dunn, C., Timothy, K., Vincent, G. M., and Leppert, M. (1991b). Consistent linkage of the long QT syndrome to the Harvey ras-1 locus on chromosome 11. Am. J. Hum. Genet. 49, 1335–1339.
Keating, M. T. (1992). Linkage analysis and long QT syndrome. Using genetics to study cardiovascular disease. Circulation 85, 1973–1986.
Kinszler, K. W., et al. (1991). Science 251, 1366–1370.
Koch, M. C., Steinmeyer, K., Lorenz, C., Ricker, K., Wolf, F., Otto, M., Zoll, B., Lehmann-Horn, F., Grzeschik, K-H., and Jentsch, T. J. (1992). The skeletal muscle chloride channel in dominant and recessive human myotonia. Science 257, 797–800.

Kohler, G. and Milstein, C. (1975). Nature 256, 495–497.
Kraemer, F. B. et al. (1993). J. Lipid Res. 34, 663–672.
Kubo, T., et al. (1988). FEBS Letts. 241, 119.
Landegren, et al. (1988). Science 242, 229.
Lathrop, G. M., Lalouel, J-M., Julier, C., and Ott, J. (1985). Multilocus linkage analysis in humans: detection of linkage and estimation of recombination. Am. J. Hum. Genet. 37, 482–498.
Lerche, H., Heine, R., Pika, U., George, A. L., Mitrovic, N., Browatzki, M., Weiss, T., River-Bastide, M., Franke, C., Lomonaco, M., Ricker, K., and Lehmann-Horn, F. (1993). Human sodium channel myotonia: slowed channel inactivation due to substitutions for a glycine within the III–IV linker. J. Physiol. 470, 13–22.
Lichter, P., Cremer, T., Borden, J., Manuelidis, L., and Ward, D. C. (1988). Delineation of individual human chromosomes in metaphase and interphase cells by in situ suppression hybridization using recombinant DNA libraries. Hum. Genet. 80, 224–234.
Lim, et al. (1992). Circulation 83, 2007–2011.

LIST OF REFERENCES (Cont'd)

Ludwig, J., Terlau, H., Wunder, F., Bruggeman, A., Pardo, L. A., Marquardt, A., Strumer, W., and Pongs, O. (1994). Functional expression of a rat homologue of the voltage gated ether a go-go potassium channel reveals differences in selectivity and activation kinetics between the Drosophila channel and its mammalian counterpart. EMBO J. 13, 4451–4458.
MacKinnon, R. (1991). Determination of the subunit stoichiometry of a voltage-activated potassium channel. Nature 350, 232–235.
MacKinnon, R., Aldrich, R. W., and Lee, A. W. (1993). Functional stoichiometry of shaker potassium channel inactivation. Science 262, 757–759.
Madzak, et al. (1992). J. Gen. Virol. 73, 1533–1536.
Magovcevic, I., Ang, S-L., Seidman, J. G., Tolman, C., Neer, E., and Mortons, C. (1992). Regional localization of the human G protein $a_{i2}$ (GNAI2) gene: Assignment to 3021 and a related sequence (GNAI2L) to 12p12-p13. Genomics 12, 125–129.
Maniatis, T. et al. (1982). Molecular Cloning: A Laboratory Manual (Cold Spring Harbor Laboratory, Cold Spring Harbor, N.Y.).
Maniatis. T., et al. (1989). Molecular Cloning: A Laboratory Manual (Cold Spring Harbor Laboratory, Cold Spring Harbor, N.Y.).
Mann and Baltimore (1985). J. Virol. 54, 401–407.
Marchuk, D., Drumm, M., Saulino, A., and Collins, F. S. (1990). Construction of T-vectors, a rapid and general system for direct cloning of unmodified PCR products. Nucl. Acids Res. 19, 1154.
Margolskee (1992). Curr. Top. Microbiol. Immunol. 158, 67–90.
Martin, R., et al. (1990). BioTechniques 9, 762–768.
Matteucci, M. D. and Caruthers, M. H. (1981). J. Am. Chem. Soc. 103, 3185.
Matthews & Kricka (1988). Anal. Biochem. 169, 1.
McClatchey, A., Lin, C., Wang, J., Hoffman, E., Rojas, C., and Gusella, J. (1992a). The genomic structure of the human skeletal muscle sodium channel gene. Hum. Mol. Genet. 1, 521–527.

LIST OF REFERENCES (Cont'd)

McClatchey, A., Van den Bergh, P., Pericak-Vance, M., Raskind, W., Verellen, C., McKenna-Yasek, D., Rao, K., Haines, J. L., Bird, T., Brown, R. H., and Gusella, J. F. (1992b). Temperature-sensitive mutations in the III–IV cytoplasmic loop region of the skeletal muscle sodium channel gene in paramyotonia congenita. Cell 68, 769–774.
McClatchey, A., McKenna-Yasek, D., Cros, D., Worthens, H. G., Kuncl, R. W., DeSilva, S. M., Cornblath, D. R., Gusella, J. F., and Brown, R. H. (1992c). Novel mutations in families with unusual and variable disorders of the skeletal muscle sodium channel. Nature Genet. 2, 148–152.
Mettlin, C., et al. (1990). American Journal of Epidemiology 131, 973–983.
Metzger, et al. (1988). Nature 334, 31–36.
Miller (1992). Curr. Top. Microbiol. Immunol. 158, 1–24.
Miller, et al. (1985). Mol. Cell. Biol. 5, 431–437.
Miller, et al. (1988). J. Virol. 62, 4337–4345.
Modrich, P. (1991). Ann. Rev. Genet. 25, 229–253.
Mombaerts, P., et al. (1992). Cell 68, 869.
Moss, A. J., Schwartz, P. J., Crampton, R. S., Tzivoni, D., Locati, E. H., MacCluer, J., Hall, W. J., Weitkamp, L., Vincent, G. M., Garson, A., Robinson, J. L., Benhorin, J., and Choi, S. (1991). The long QT syndrome: prospective longitudinal study of 328 families. Circulation 84, 1136–1144.
Moss (1992). Curr. Top. Microbiol. Immunol. 158, 25–38.
Muzyczka (1992). Curr. Top. Microbiol. Immunol. 158, 97–123.
Nabel, et al. (1990). Science 249, 1285–1288.
Nabel (1992). Hum. Gene Ther. 3, 399–410.
Newton, C. R., Graham, A., Heptinstall, L. E., Powell, S. J., Summers, C., Kalsheker, N., Smith, J. C., and Markham, A. F. (1989). Nucl. Acids Res. 17, 2503–2516.
Nguyen, Q., et al. (1992). BioTechniques 13, 116–123.
Novack, et al. (1986). Proc. Natl. Acad. Sci. USA 83, 586.
Ohi, et al. (1990). Gene 89, 279–282.

LIST OF REFERENCES (Cont'd)

Orita, M., Iwahana, H., Kanazawa, H., and Sekiya, T. (1989). Detection of polymorphisms of human DNA by gel electrophoresis as single strand conformation polymorphisms. Proc. Natl. Acad. Sci. USA 86, 2766–2770.
Page, et al. (1990). J. Virol. 64, 5370–5276.
Pellicer, et al. (1980). Science 209, 1414–1422.
Petropoulos, et al. (1992). J. Virol. 66, 3391–3397.
Philpott, K. L., et al. (1992). Science 256, 1448.
Ptacek, L. J., George, A. L., Griggs, R. C., Tawil, R., Kallen, R. G., Barchi, R. L., Robertson, M., and Leppert, M. F. (1991). Identification of a mutation in the gene causing hyperkalemic periodic paralysis. Cell 67, 1021–1027.
Ptacek, L. J., George, A. L., Barchi, R., Griggs, R., Riggs, J., Robertson, M., Leppert, M. (1992). Mutations in an S4 segment of the adult skeletal muscle sodium channel cause paramyotonia congenita. Neuron 8, 891–897.
Quantin, et al. (1992). Proc. Natl. Acad. Sci. USA 89, 2581–2584.
Rano & Kidd (1989). Nucl. Acids Res. 17, 8392.
Rigby, P. W. J., et al. (1977). J. Mol. Biol. 113, 237–251.
Rojas, C., Wang, J., Schwartz, L. S., Hoffman, E. P., Powell, B. R., and Brown R. H. (1991). A met-to-val mutation in the skeletal muscle $Na^+$ channel α-subunit in hyperkalaemic periodic paralysis. Nature 354, 387–389.
Romano, C. (1965). Congenital cardiac arrhythmia. Lancet I658–659.

Rosenfeld, et al. (1992). Cell 68, 143–155.

Roy, N., Kahlem, P., Dausse, E., Bennaceur, M., Faure, S., Weissenbach, J., Komajda, M., Denjoy, I., Coumel, P., Schwartz, K., and Guicheney, P. (1994). Exclusion of HRAS from long QT locus. Nat. Genet. 8, 113–114.

Rudolph, J. A., Spier, S. J., Byrns, G., Rojas, C. V., Bernoco, D., and Hoffman, E. P. (1992). Periodic paralysis in quarter horses: a sodium channel mutation disseminated by selective breeding. Nature Genet. 2, 144–147.

Sambrook, J., et al. (1989). Molecular Cloning: A Laboratory Manual, 2nd Ed. (Cold Spring Harbor Laboratory, Cold Spring Harbor, N.Y.).

LIST OF REFERENCES (Cont'd)

Schwartz, P. J., Periti, M., and Malliani, A. (1975). The long QT syndrome. Am. Heart J. 109, 378–390.

Schwartz, P. J., Locati, E. H., Napolitano, C., and S. G. Priori (1994). The long QT syndrome. In Cardiac Electrophysiology: from cell to bedside. D. P. Zipes and J. Jalife eds. (W. B. Sanders Company) pp.788–811.

Seino, S., Yamada, Y., Espinosa, R., LeBeau, M., and Bell, G. (1992). Assignment of the gene encoding the $\alpha_1$ subunit of the neuroendocrine/brain-type calcium channel (CACNL1A2) to human chromosome 3, band p14.3. Genomics 13, 1375–1377.

Sheffield, V. C., et al. (1989). Proc. Natl. Acad. Sci. USA 86, 232–236.

Sheffield, V. C., et al., 1991. Am. J. Hum. Genet. 49, 699–706.

Shimada, et al. (1991). J. Clin. Invest. 88, 1043–1047.

Shinkai, Y., et al. (1992). Cell 68, 855.

Snouwaert, J. N., et al. (1992). Science 257, 1083.

Sorge, et al. (1984). Mol. Cell. Biol. 4, 1730–1737.

Sternberg, N. (1990). Bacteriophage P1 cloning system for the isolation, amplification, and recovery of DNA fragments as large as 100 kilobase pairs. Proc. Natl. Acad. Sci. USA 87, 103–107.

Stewart, et al. (1992). Hum. Gene Ther. 3, 267–275.

Stratford-Perricaudet, et al. (1990). Hum. Gene Ther. 1, 241–256.

Stuhmer, W., Conti, F., Suzuki, H., Wang, X., Noda, M., Yahagi, N., Kubo, H., Numa, S. (1989). Structural parts involved in activation and inactivation of the sodium channel. Nature 339, 597–603.

Surawicz, B. (1989). Electrophysiologic substrate of torsade de pointes: Dispersion of repolarization or early afterdepolarizations? J. Am. Coll. Cardiol. 14, 172–184.

Towbin, J. A., Li, H., Taggart, T., Lehmann, M. H., Schwartz, P. J., Satler, C. A., Ayyagari, R., Robinson, J. L., Moss, A., and Hejtmancik, F. (1994). Evidence of genetic heterogeneity in Romano-Ward long QT syndrome (LQTs): Analysis of 23 families. Circulation 90, 2635–2644.

LIST OF REFERENCES (Cont'd)

Temple, B. L., Papazian, T. L., Schwarz, T. L., Jan, Y. N., and Jan, L. Y. (1987). Sequence of a probable potassium channel component encoded at Shaker locus of Drosophila. Science 237, 770–775.

Valancius, V. & Smithies, O. (1991). Mol. Cell Biol. 11, 1402.

Vincent, G. M., Timothy, K. W., Leppert, M. F., and Keating, M. T. (1992). The spectrum of symptoms and QT intervals in carriers of the gene for the long QT syndrome. N. Engl. J. Med. 327, 846–852.

Wagner, et al. (1991). Proc. Natl. Acad. Sci. USA 88, 4255–4259.

Wagner, et al. (1990). Proc. Natl. Acad. Sci. USA 87, 3410–3414.

Wang and Huang (1989). Biochemistry 28, 9508–9514.

Wang, Q. and Keating, M. T. (1994). Isolation of P1 insert ends by direct sequencing. BioTechniques 17, 282–284.

Ward, O. C. (1964). A new familial cardiac syndrome in children. J. Ir. Med. Assoc. 54, 103–106.

Warmke, J. E. and Ganetzky, B. (1994). A family of potassium channel genes related to eag in Drosophila and mammals. Proc. Natl. Acad. Sci. 91, 3438–3442.

Wartell, R. M., et al. (1990). Nucl. Acids Res. 18, 2699–2705.

Weinstein, L. S., Speigel, A. M., Carter, A. D. (1988). Cloning and characterization of the human gene for the $\alpha$-subunit of $G_{i2}$, a GTP-binding signal transduction protein. FEBS Letters 232, 333–340.

West, J., Patton, D., Scheuer, T., Wang, Y., Goldin, A., and Catterall, W. (1992). A cluster of hydrophobic amino acid residues required for fast $Na^+$-channel inactivation. Proc. Natl. Acad. Sci. USA 89, 10910–10914.

Wetmur & Davidson (1968). J. Mol. Biol. 31, 349–370.

White, M. B., et al. (1992). Genomics 12, 301–306.

Wilkinson, et al. (1992). Nucleic Acids Res. 20, 2233–2239.

Willich, S. N., Levy, D., Rocco, M. B., Tofier, G. H., Stone, P. H., and Muller, J. O. E. (1987). Circadian variation in the incidence of sudden cardiac death in the Framingham heart study population. Am. J. Cardiol. 60, 801–806.

LIST OF REFERENCES (Cont'd)

Wolff, et al. (1990). Science 247, 1465–1468.

Wolff, et al. (1991). BioTechniques 11, 474–485.

Wu, et al. (1989). J. Biol. Chem. 264, 16985–16987.

Wu, et al. (1991). J. Biol. Chem. 266, 14338–14342.

Yang, N., Ji, S., Shou, M., Ptacek, L., Barchi, R., Horn, R., George, A. (1994). Sodium channel mutations in paramyotonia congenita exhibit similar biophysical phenotypes in vitro. Proc. Natl. Acad. Sci. USA 91, 12785–12789.

Zenke, et al. (1990). Proc. Natl. Acad. Sci. USA 87, 3655–3659.

Zipes, D. P. (1987). Proarrhythmic effects of antiarrhythmic drugs. Am. J. Cardiol. 59, 26E–31E.

Patents and Patent Applications:

European Patent Application Publication No. 0332435.
EPO Publication No. 225,807.
Hitzeman et al., EP 73,675A.
PCT published application WO 93/07282.
U.S. Pat. No. 4,376,110.
U.S. Pat. No. 4,486,530.
U.S. Pat. No. 4,868,105.
U.S. Pat. No. 5,252,479.

What is claimed is:

1. A nucleic acid probe which will hybridize to a DNA coding for SCN5A polypeptide containing a mutation which causes long QT syndrome, said mutation being either an alteration of or deletion of any one or more of amino acid residues 1505, 1506 or 1507 of the SCN5A polypeptide but will not hybridize to DNA encoding wild type SCN5A under hybridization conditions which only permit hybridization products to form which are fully complementary in the region of the mutation.

2. A method for diagnosing a polymorphism which causes long QT syndrome comprising hybridizing the probe of claim 1 to a patient's sample of DNA or RNA under conditions which only permit hybridization products which are fully complementary in the region of the mutation to form and determining the presence or absence of a signal indicating a hybridization product, the presence of a hybridization signal indicating the presence of long QT syndrome.

3. A method according to claim 2 wherein the patient's DNA or RNA has been amplified and said amplified DNA or RNA is hybridized with said probe.

4. A method according to claim 3 wherein hybridization is performed in situ.

5. A nucleic acid probe which will hybridize to a DNA coding for SCN5A polypeptide containing a mutation which causes long QT syndrome said mutation being a deletion of any one or more of amino acid residues 1505, 1506 or 1507 of the SCN5A polypeptide, but will not hybridize to DNA encoding wild type SCN5A under hybridization conditions which only permit hybridization products to form which are fully complementary in the region of the mutation.

6. A method for diagnosing a polymorphism which causes long QT syndrome comprising hybridizing the probe of claim 5 to a patient's sample of DNA or RNA under conditions which only permit hybridization products which are fully complementary in the region of the mutation to form and determining the presence or absence of a signal indicating a hybridization product, the presence of a hybridization signal indicating the presence of long QT syndrome.

7. A method according to claim 6 wherein the patient's DNA or RNA has been amplified an said amplified DNA or RNA is hybridized with said probe.

8. A method according to claim 6 wherein hybridization is performed in situ.

9. A method for diagnosing a polymorphism which causes long QT syndrome comprising amplifying the region of the SCN5A gene or RNA encoding amino acids 1505–1507 of the SCN5A polypeptide, measuring the size of the amplified region, and determining whether a deletion has occurred, wherein the presence of said deletion is indicative of long QT syndrome.

10. The method of claim 9 wherein primers corresponding to SEQ ID NO.40 AND 41 are used to amplify said region of the SCN5A gene.

11. The method of claim 1o wherein the presence of a 9 base pair deletion is indicative of long QT syndrome.

12. A method for diagnosing a polymorphism which causes long QT syndrome, said polymorphism being a mutation causing an alteration of or deletion of any one or more of amino acid residues 1505, 1506 or 1507 of the SCN5A polypeptide, said method comprising using a single-stranded conformation polymorphism technique to assay for said polymorphism.

13. The method of claim 12 wherein primers corresponding to SEQ ID NOS. 40 and 41 are used.

14. The method of claim 13 wherein the presence of a 9 base pair deletion is determined, and wherein the presence of said 9 base pair deletion is indicative of long QT syndrome.

15. A method for diagnosing a polymorphism which causes long QT syndrome comprising amplifying the region of the SCN5A gene or RNA encoding amino acids 1505–1507 of the SCN5A polypeptide and sequencing the amplified gene or RNA wherein an alteration in, or a deletion of, the DNA or RNA which results in an alteration or deletion of any one or more of amino acid residues 1505–1507 is indicative of long QT syndrome.

16. A method for diagnosing a polymorphism which causes long QT syndrome comprising identifying a mismatch between a patient's DNA or RNA and a wild-type DNA or RNA probe wherein said probe hybridizes to the region of DNA encoding amino acid residues 1505–1507 of the SCN5A polypeptide.

17. The method of claim 16 wherein the mismatch is identified by an RNase assay.

18. A method according to claim 17 wherein the patient's DNA, or RNA, has been amplified and said amplified DNA, or RNA, is hybridized with said probe.

19. A method according to claim 18 wherein hybridization is performed in situ.

20. A nucleic acid probe which will hybridize to DNA coding for a mutant HERG polypeptide containing a mutation which causes long QT syndrome under conditions which only permit hybridization products to form which are fully complementary in the region causing said mutation, said mutation being caused by a mutation in said DNA selected from the group consisting of a deletion comprising bases 1498–1524, a deletion of base 1261, the presence of a T rather than a C at base position 1682, the presence of a G rather than an A at base position 1408, the presence of an A rather than a G at base position 1882, and the presence of a C rather than a G at the start of the splice donor site of intron III, but will not hybridize to DNA encoding wild type HERG.

21. A method for diagnosing a mutation which causes long QT syndrome comprising hybridizing, under conditions which only permit hybridization products to form which are fully complementary in the region causing said mutation, a probe of claim 20 to a patient's sample of DNA or RNA and determining the presence or absence of a signal indicating a hybridization product, the presence of a hybridization signal is indicative of long QT syndrome.

22. A method for diagnosing a mutation which causes long QT syndrome comprising:

a) amplifying the region of HERG gene DNA, or RNA, which encodes amino acids 500–508 of the HERG polypeptide, b) measuring the size of the amplified region, and c) determining whether a deletion has occurred, wherein the presence of said deletion is indicative of long QT syndrome.

23. The method of claim 22 wherein primers corresponding to SEQ ID NOS. 23 and 28 are used to amplify said region of the HERG gene.

24. The method of claim 23 wherein the presence of a 27 base pair deletion is indicative of long QT syndrome.

25. A method for diagnosing a polymorphism which causes long QT syndrome comprising amplifying the region of the HERG gene or RNA surrounding base position 1261 and determining whether a deletion has occurred, said deletion being indicative of long QT syndrome.

26. The method of claim 25 wherein primers corresponding to SEQ ID NOS. 21 and 29 are used to amplify said region of the HERG gene.

27. The method of claim 26 wherein the presence of a 1 base pair deletion is indicative of long QT syndrome.

28. A method for diagnosing a mutation which causes long QT syndrome, said polymorphism being a member of the group consisting of a deletion of bases 1498–1524 of HERG, a deletion of base 1261 of HERG, a T rather than a C at base 1682 of HERG, a G rather than an A at base 1408 of HERG, an A rather than a G at base 1882 of HERG, and a C rather than a G at the start of the splice donor site of intron III of HERG, said method comprising using a single-stranded conformation polymorphism technique to assay for said mutation.

29. A method according to claim 28 wherein a primer pair selected from the group consisting of (i) SEQ ID NOS.: 23 and 29; (ii) SEQ ID NOS.: 23 and 28; (iii) SEQ ID NOS.: 21 and 29; (iv) SEQ ID NOS.: 25 and 31; and SEQ ID NOS.: 24 and 32 is used.

30. A method for diagnosing a mutation which causes long QT syndrome comprising amplifying a region of the HERG gene or RNA and sequencing the amplified gene or RNA wherein long QT syndrome is indicated by any one or more mutations of the following group: a deletion comprising base pairs 1498–1524, a deletion consisting of base pair 1261, a T at base position 1682, a G at base position 1408, a C at the start of the splice donor of intron III, and an A at base position 1882.

31. A method of diagnosing a mutation which causes long QT syndrome comprising identifying a mismatch between a patient's DNA or RNA of the HERG gene and a wild-type DNA or RNA probe wherein said probe selectively hybridized to a region of DNA or RNA of the HERG gene wherein said region is any one of the following group: a region comprising bases 1498–1524, a region comprising base 1261, a region comprising base 1682, a region comprising base 1408, a region comprising base 1882, and a region comprising the splice donor site of intron III.

32. The method of claim 31 wherein the mismatch is identified by an RNase assay.

* * * * *

SEQUENCE LISTING ( 1 ) GENERAL INFORMATION:

( i i i ) NUMBER OF SEQUENCES: 81

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:1:

ACTTTCATCG TACTGAATAA AGGCAA 26

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:2:

GAGTGAACCA GAATCTTCAC AGC 23

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:3:

GGACCGTGAG TCCATCGTGT GA 22

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO (vi) ORIGINAL SOURCE:
    (A) ORGANISM: Homo sapiens (xi) SEQUENCE DESCRIPTION: SEQ ID NO:4:

AGCCCATTCA CAACATATAC AGTCT    25

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:5:

AGCAACTTCA TCCCAGCTGC TGAG    24

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:6:

CTCCCAGCAT CTCAGGTCAA GTG    23

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:7:

TATGAAGAGC AGCCTCAGTG GGAA    24

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (v i) ORIGINAL SOURCE:
   (A) ORGANISM: Homo sapiens (x i) SEQUENCE DESCRIPTION: SEQ ID NO:8:

CTTTTTCTTC TGTTGGTTGA AGTTG                                           25

(2) INFORMATION FOR SEQ ID NO:9:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (i i) MOLECULE TYPE: cDNA (i i i) HYPOTHETICAL: NO (v i) ORIGINAL SOURCE:
      (A) ORGANISM: Homo sapiens (x i) SEQUENCE DESCRIPTION: SEQ ID NO:9:

TTAGGGGGCC AGGACATCTT C                                               21

(2) INFORMATION FOR SEQ ID NO:10:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (i i) MOLECULE TYPE: cDNA (i i i) HYPOTHETICAL: NO (v i) ORIGINAL SOURCE:
      (A) ORGANISM: Homo sapiens (x i) SEQUENCE DESCRIPTION: SEQ ID NO:10:

CAGGGGCCGT GGGATGGGCT TCTGG                                           25

(2) INFORMATION FOR SEQ ID NO:11:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (i i) MOLECULE TYPE: cDNA (i i i) HYPOTHETICAL: NO (v i) ORIGINAL SOURCE:
      (A) ORGANISM: Homo sapiens (x i) SEQUENCE DESCRIPTION: SEQ ID NO:11:

CACCATATTC AAGCAGATCA G                                               21

(2) INFORMATION FOR SEQ ID NO:12:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (i i) MOLECULE TYPE: cDNA (i i i) HYPOTHETICAL: NO ( v i ) ORIGINAL SOURCE:
    ( A ) ORGANISM: Homo sapiens ( x i ) SEQUENCE DESCRIPTION: SEQ ID NO:12:

CTGCGCCACT ACTACTTCAC C                        21

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:13:

GCTGGGCCGC TCCCCTTGGA                          20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:14:

GCATCTTCAT TAATTATTCA                          20

( 2 ) INFORMATION FOR SEQ ID NO:15:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:15:

AGGAGGTGGG G                                   11

( 2 ) INFORMATION FOR SEQ ID NO:16:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (v i) ORIGINAL SOURCE:
    (A) ORGANISM: Homo sapiens (x i) SEQUENCE DESCRIPTION: SEQ ID NO:16:

CCCCAGCTGA TC                                                                                      12

(2) INFORMATION FOR SEQ ID NO:17:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (v i) ORIGINAL SOURCE:
        (A) ORGANISM: Homo sapiens (x i) SEQUENCE DESCRIPTION: SEQ ID NO:17:

TGGCTGTGAG T                                                                                       11

(2) INFORMATION FOR SEQ ID NO:18:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (v i) ORIGINAL SOURCE:
        (A) ORGANISM: Homo sapiens (x i) SEQUENCE DESCRIPTION: SEQ ID NO:18:

CCCCAGCCCT C                                                                                       11

(2) INFORMATION FOR SEQ ID NO:19:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (v i) ORIGINAL SOURCE:
        (A) ORGANISM: Homo sapiens (x i) SEQUENCE DESCRIPTION: SEQ ID NO:19:

CCTGGGTATG G                                                                                       11

(2) INFORMATION FOR SEQ ID NO:20:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO ( v i ) ORIGINAL SOURCE:
    ( A ) ORGANISM: Homo sapiens ( x i ) SEQUENCE DESCRIPTION: SEQ ID NO:20:

CTCCAGGGAA G                                                                                                11

( 2 ) INFORMATION FOR SEQ ID NO:21:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:21:

GACGTGCTGC CTGAGTACAA                                                                                       20

( 2 ) INFORMATION FOR SEQ ID NO:22:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:22:

TTCCTGCTGA AGGAGACGGA AG                                                                                    22

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:23:

ACCACCTACG TCAATGCCAA C                                                                                     21

( 2 ) INFORMATION FOR SEQ ID NO:24:

( i ) SEQUENCE CHARACTERISTICS:
        ( A ) LENGTH: 21 base pairs
        ( B ) TYPE: nucleic acid
        ( C ) STRANDEDNESS: single (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Homo sapiens (xi) SEQUENCE DESCRIPTION: SEQ ID NO:24:

TGCCCCATCA ACGGAATGTG C           21

(2) INFORMATION FOR SEQ ID NO:25:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:25:

GATCGCTACT CAGAGTACG           19

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:26:

GCCTGGGCGG CCCCTCCATC AA           22

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO:27:

CACCTCCTCG TTGGCATTGA C           21

( 2 ) INFORMATION FOR SEQ ID NO:28:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( A ) ORGANISM: Homo sapiens ( x i ) SEQUENCE DESCRIPTION: SEQ ID NO:28:

GTCGAAGGGG ATGGCGGCCA CCATG                       25

( 2 ) INFORMATION FOR SEQ ID NO:29:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( A ) ORGANISM: Homo sapiens ( x i ) SEQUENCE DESCRIPTION: SEQ ID NO:29:

TACACCACCT GCCTCCTTGC TGA                         23

( 2 ) INFORMATION FOR SEQ ID NO:30:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( A ) ORGANISM: Homo sapiens ( x i ) SEQUENCE DESCRIPTION: SEQ ID NO:30:

GCCGCGCCGT ACTCTGAGTA G                           21

( 2 ) INFORMATION FOR SEQ ID NO:31:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (i v) ANTI-SENSE: YES (v i) ORIGINAL SOURCE:
    (A) ORGANISM: Homo sapiens (x i) SEQUENCE DESCRIPTION: SEQ ID NO:31:

CAGCCAGCCG ATGCGTGAGT CCA                    23

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: YES (v i) ORIGINAL SOURCE:
        (A) ORGANISM: Homo sapiens (x i) SEQUENCE DESCRIPTION: SEQ ID NO:32:

GCCCGCCCCT GGGCACACTC A                      21

(2) INFORMATION FOR SEQ ID NO:33:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: YES (v i) ORIGINAL SOURCE:
        (A) ORGANISM: Homo sapiens (x i) SEQUENCE DESCRIPTION: SEQ ID NO:33:

CAGCATCTGT GTGTGGTAG                         19

(2) INFORMATION FOR SEQ ID NO:34:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: YES (v i) ORIGINAL SOURCE:
        (A) ORGANISM: Homo sapiens (x i) SEQUENCE DESCRIPTION: SEQ ID NO:34:

GGCATTTCCA GTCCAGTGC                         19

(2) INFORMATION FOR SEQ ID NO:35:

(i) SEQUENCE CHARACTERISTICS:
        (A) LENGTH: 20 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:35:

CCTGGCCATG AAGTTCAAGA                                        20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:36:

GCACTGCAAA CCCTTCCGAG                                        20

(2) INFORMATION FOR SEQ ID NO:37:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vi) ORIGINAL SOURCE:
        (A) ORGANISM: Homo sapiens (xi) SEQUENCE DESCRIPTION: SEQ ID NO:37:

GTCGGAGAAC TCAGGGTACA TG                                     22

(2) INFORMATION FOR SEQ ID NO:38:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (xi) SEQUENCE DESCRIPTION: SEQ ID NO:38:

GCCTGTCTGA TCTCCCTGTG TGA                                                           23

( 2 ) INFORMATION FOR SEQ ID NO:39:

( i ) SEQUENCE CHARACTERISTICS:
          ( A ) LENGTH: 23 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
          ( A ) ORGANISM: Homo sapiens ( x i ) SEQUENCE DESCRIPTION: SEQ ID NO:39:

ACCCAGCCCA GTGGGGAGCT GGT                                                           23

( 2 ) INFORMATION FOR SEQ ID NO:40:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
          ( A ) ORGANISM: Homo sapiens ( x i ) SEQUENCE DESCRIPTION: SEQ ID NO:40:

CCATGCTGGG GCCTCTAAAA CC                                                            22

( 2 ) INFORMATION FOR SEQ ID NO:41:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
          ( A ) ORGANISM: Homo sapiens ( x i ) SEQUENCE DESCRIPTION: SEQ ID NO:41:

GGCTCTGATG GCTGGCCATG TG                                                            22

( 2 ) INFORMATION FOR SEQ ID NO:42:

( i ) SEQUENCE CHARACTERISTICS:
          ( A ) LENGTH: 22 base pairs
          ( B ) TYPE: nucleic acid
          ( C ) STRANDEDNESS: single
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Homo sapiens ( x i ) SEQUENCE DESCRIPTION: SEQ ID NO:42:

CCCAGCGAGC ACTTTCCATT TG　　　　　　　　　　　　　　　　　　　　　　　　　22

( 2 ) INFORMATION FOR SEQ ID NO:43:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( A ) ORGANISM: Homo sapiens ( x i ) SEQUENCE DESCRIPTION: SEQ ID NO:43:

GCTTCTCCGT CCAGCTGACT TGTA　　　　　　　　　　　　　　　　　　　　　　　24

( 2 ) INFORMATION FOR SEQ ID NO:44:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:44:

GAGCCCAGCC GTGGGCATCC T　　　　　　　　　　　　　　　　　　　　　　　　21

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( v i ) ORIGINAL SOURCE:
        ( A ) ORGANISM: Homo sapiens ( x i ) SEQUENCE DESCRIPTION: SEQ ID NO:45:

GTCCCCACTC ACCATGGGCA G　　　　　　　　　　　　　　　　　　　　　　　　21

( 2 ) INFORMATION FOR SEQ ID NO:46:

( i ) SEQUENCE CHARACTERISTICS:
   ( A ) LENGTH: 53 amino acids
   ( B ) TYPE: amino acid
   ( D ) TOPOLOGY: linear ( i i ) MOLECULE TYPE: peptide ( i i i ) HYPOTHETICAL: NO ( v i ) ORIGINAL SOURCE:
   ( A ) ORGANISM: Homo sapiens ( x i ) SEQUENCE DESCRIPTION: SEQ ID NO:46:

| Asp | Asn | Phe | Asn | Gln | Gln | Lys | Lys | Lys | Leu | Gly | Gly | Gln | Asp | Ile | Phe |
|---|---|---|---|---|---|---|---|---|---|---|---|---|---|---|---|
| 1 | | | | 5 | | | | | 10 | | | | | 15 | |
| Met | Thr | Glu | Glu | Gln | Lys | Lys | Tyr | Tyr | Asn | Ala | Met | Lys | Lys | Leu | Gly |
| | | | 20 | | | | | 25 | | | | | 30 | | |
| Ser | Lys | Lys | Pro | Gln | Lys | Pro | Ile | Pro | Arg | Pro | Leu | Asn | Lys | Tyr | Gln |
| | | 35 | | | | | 40 | | | | | 45 | | | |
| Gly | Phe | Ile | Phe | Asp | | | | | | | | | | | |
| | | | 50 | | | | | | | | | | | | |

( 2 ) INFORMATION FOR SEQ ID NO:47:

( i ) SEQUENCE CHARACTERISTICS:
   ( A ) LENGTH: 53 amino acids
   ( B ) TYPE: amino acid
   ( D ) TOPOLOGY: linear ( i i ) MOLECULE TYPE: peptide ( i i i ) HYPOTHETICAL: NO ( v i ) ORIGINAL SOURCE:
   ( A ) ORGANISM: Homo sapiens ( x i ) SEQUENCE DESCRIPTION: SEQ ID NO:47:

| Asp | Asn | Phe | Asn | Gln | Gln | Lys | Lys | Lys | Leu | Gly | Gly | Lys | Asp | Ile | Phe |
|---|---|---|---|---|---|---|---|---|---|---|---|---|---|---|---|
| 1 | | | | 5 | | | | | 10 | | | | | 15 | |
| Met | Thr | Glu | Glu | Gln | Lys | Lys | Tyr | Tyr | Asn | Ala | Met | Lys | Lys | Leu | Gly |
| | | | 20 | | | | | 25 | | | | | 30 | | |
| Ser | Lys | Lys | Pro | Gln | Lys | Pro | Ile | Pro | Arg | Pro | Gln | Asn | Lys | Ile | Gln |
| | | 35 | | | | | 40 | | | | | 45 | | | |
| Gly | Met | Val | Tyr | Asp | | | | | | | | | | | |
| | | | 50 | | | | | | | | | | | | |

( 2 ) INFORMATION FOR SEQ ID NO:48:

( i ) SEQUENCE CHARACTERISTICS:
   ( A ) LENGTH: 53 amino acids
   ( B ) TYPE: amino acid
   ( D ) TOPOLOGY: linear ( i i ) MOLECULE TYPE: peptide ( i i i ) HYPOTHETICAL: NO ( v i ) ORIGINAL SOURCE:
   ( A ) ORGANISM: Homo sapiens ( x i ) SEQUENCE DESCRIPTION: SEQ ID NO:48:

| Asp | Asn | Phe | Asn | Gln | Gln | Lys | Lys | Lys | Phe | Gly | Gly | Gln | Asp | Ile | Phe |
|---|---|---|---|---|---|---|---|---|---|---|---|---|---|---|---|
| 1 | | | | 5 | | | | | 10 | | | | | 15 | |
| Met | Thr | Glu | Glu | Gln | Lys | Lys | Tyr | Tyr | Asn | Ala | Met | Lys | Lys | Leu | Gly |
| | | | 20 | | | | | 25 | | | | | 30 | | |
| Ser | Lys | Lys | Pro | Gln | Lys | Pro | Ile | Pro | Arg | Pro | Ala | Asn | Lys | Phe | Gln |
| | | 35 | | | | | 40 | | | | | 45 | | | |

Gly Met Val Phe Asp
    50

( 2 ) INFORMATION FOR SEQ ID NO:49:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:49:

Asp Asn Phe Asn Gln Gln Lys Lys Lys Phe Gly Gly Lys Asp Ile Phe
1               5                   10                  15

Met Thr Glu Glu Gln Lys Lys Tyr Tyr Asn Ala Met Lys Lys Leu Gly
            20                  25                  30

Ser Lys Lys Pro Gln Lys Pro Ile Pro Arg Pro Gln Asn Lys Ile Gln
        35                  40                  45

Gly Met Val Tyr Asp
    50

( 2 ) INFORMATION FOR SEQ ID NO:50:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:50:

Asp Asn Phe Asn Gln Gln Lys Lys Lys Phe Gly Gly Gln Asp Ile Phe
1               5                   10                  15

Met Thr Glu Glu Gln Lys Lys Tyr Tyr Asn Ala Met Lys Lys Leu Gly
            20                  25                  30

Ser Lys Lys Pro Gln Lys Pro Ile Pro Arg Pro Ala Asn Lys Phe Gln
        35                  40                  45

Gly Met Val Phe Asp
    50

( 2 ) INFORMATION FOR SEQ ID NO:51:

( i ) SEQUENCE CHARACTERISTICS:
        ( A ) LENGTH: 53 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:51:

Asp Asn Phe Asn Gln Gln Lys Lys Lys Phe Gly Gly Gln Asp Ile Phe
1               5                   10                  15

Met Thr Glu Glu Gln Lys Lys Tyr Tyr Asn Ala Met Lys Lys Leu Gly
            20                  25                  30

Ser Lys Lys Pro Gln Lys Pro Ile Pro Arg Pro Gly Asn Lys Phe Gln
        35                  40                  45

Gly Met Val Phe Asp (2) INFORMATION FOR SEQ ID NO:52:

(i) SEQUENCE CHARACTERISTICS:
        (A) LENGTH: 53 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (A) ORGANISM: Fugu rubripes (xi) SEQUENCE DESCRIPTION: SEQ ID NO:52:

```
Asp Asn Phe Asn Gln Gln Lys Lys Lys Phe Gly Gly Gln Asp Ile Phe
1               5                   10                  15
Met Thr Glu Glu Gln Lys Lys Tyr Tyr Asn Ala Met Lys Lys Leu Gly
            20                  25                  30
Ser Lys Lys Pro Gln Lys Pro Ile Pro Arg Pro Gln Asn Lys Ile Gln
        35                  40                  45
Gly Met Val Phe Asp
        50
```

(2) INFORMATION FOR SEQ ID NO:53:

(i) SEQUENCE CHARACTERISTICS:
        (A) LENGTH: 54 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (A) ORGANISM: Loligo opalescens (xi) SEQUENCE DESCRIPTION: SEQ ID NO:53:

```
Asp Asn Phe Asn Gln Gln Lys Lys Gly Ala Gly Gly Ser Leu Glu Val
1               5                   10                  15
Phe Met Thr Asp Asp Gln Lys Lys Tyr Tyr Lys Ala Met Lys Asn Leu
            20                  25                  30
Gln Ser Lys Lys Pro Thr Lys Gly Ile Pro Met Pro Gly Phe Lys Ile
        35                  40                  45
Ala Glu Trp Met Phe His
        50
```

(2) INFORMATION FOR SEQ ID NO:54:

(i) SEQUENCE CHARACTERISTICS:
        (A) LENGTH: 55 amino acids
        (B) TYPE: amino acid
        (D) TOPOLOGY: linear (ii) MOLECULE TYPE: peptide (iii) HYPOTHETICAL: NO (vi) ORIGINAL SOURCE:
        (A) ORGANISM: Loligo bleekiri (xi) SEQUENCE DESCRIPTION: SEQ ID NO:54:

```
Asp Lys Phe Ser Phe Leu Lys Lys Lys Tyr Asp Gly Thr Tyr Leu Asp
1               5                   10                  15
```

```
    Met  Phe  Leu  Thr  Pro  Thr  Gln  Gln  Asn  Tyr  Tyr  Asn  Thr  Leu  Lys  Lys
                   20                  25                            30

Leu  Gly  Thr  Lys  Lys  Pro  Gln  Lys  Thr  Val  Lys  Arg  Pro  Lys  Asn  Lys
                   35                  40                            45

Cys  Gln  Ala  Val  Val  Tyr  Asp
                   50                  55
```

( 2 ) INFORMATION FOR SEQ ID NO:55:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Drosophila melanogaster ( x i ) SEQUENCE DESCRIPTION: SEQ ID NO:55:

```
    Asp  Asn  Phe  Asn  Met  Leu  Arg  Arg  Ser  Ile  Glu  Gly  Val  Leu  Glu  Met
    1              5                        10                            15

Phe  Leu  Thr  Glu  Ser  Gln  Lys  His  Tyr  Tyr  Thr  Ala  Met  Lys  Lys  Leu
                   20                  25                            30

Gly  Arg  Lys  Lys  Pro  Gln  Lys  Val  Ile  Lys  Arg  Pro  Ile  Asn  His  Phe
                   35                  40                            45

Leu  Ala  Met  Phe  Tyr  Asp
                   50
```

( 2 ) INFORMATION FOR SEQ ID NO:56:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Heliothis virescens ( x i ) SEQUENCE DESCRIPTION: SEQ ID NO:56:

```
    Asp  Asn  Phe  Asn  Glu  Gln  Lys  Lys  Lys  Ala  Ala  Gly  Ser  Leu  Glu  Met
    1              5                        10                            15

Phe  Met  Thr  Glu  Asp  Gln  Lys  Lys  Tyr  Tyr  Asn  Ala  Met  Lys  Lys  Met
                   20                  25                            30

Gly  Ser  Lys  Lys  Pro  Leu  Lys  Ala  Ile  Pro  Arg  Pro  Lys  Trp  Arg  Pro
                   35                  40                            45

Gln  Ala  Ile  Val  Phe  Glu
                   50
```

( 2 ) INFORMATION FOR SEQ ID NO:57:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:57:

Gly Ser Lys Lys Pro Gln Lys Pro Ile Pro
    1               5                   10

( 2 ) INFORMATION FOR SEQ ID NO:58:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:58:

GGCTCCAAGA AGCCCCAGAA GCCCATCCC                                                    29

( 2 ) INFORMATION FOR SEQ ID NO:59:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:59:

Gly Ser Lys Lys Pro Ile Pro
    1               5

( 2 ) INFORMATION FOR SEQ ID NO:60:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:60:

GGCTCCAAGA AGCCCATCCC                                                              20

( 2 ) INFORMATION FOR SEQ ID NO:61:

( i ) SEQUENCE CHARACTERISTICS:
        ( A ) LENGTH: 45 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:61:

TGGTTCCTCA TCGACATGGT GGCCGCCATC CCCTTCGACC TGCTC 45

( 2 ) INFORMATION FOR SEQ ID NO:62:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:62:

```
Trp Phe Leu Ile Asp Met Val Ala Ala Ile Pro Phe Asp Leu Leu
1               5                   10                  15
```

( 2 ) INFORMATION FOR SEQ ID NO:63:

( i ) SEQUENCE CHARACTERISTICS:
        ( A ) LENGTH: 54 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:63:

GTCATCTACA CGGCTGTCTT CACACCCTAC TCGGCTGCCT TCCTGCTGAA GGAG 54

( 2 ) INFORMATION FOR SEQ ID NO:64:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: peptide ( i i i ) HYPOTHETICAL: NO ( v i ) ORIGINAL SOURCE:
        ( A ) ORGANISM: Homo sapiens ( x i ) SEQUENCE DESCRIPTION: SEQ ID NO:64:

```
Val Ile Tyr Thr Ala Val Phe Thr Pro Tyr Ser Ala Ala Phe Leu Leu
1               5                   10                  15
Lys Glu
```

( 2 ) INFORMATION FOR SEQ ID NO:65:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( v i ) ORIGINAL SOURCE:

(A) ORGANISM: Homo sapiens (x i) SEQUENCE DESCRIPTION: SEQ ID NO:65:

GTCATCTACC GGCTGTCTTC ACACCCTACT CGGCTGCCTT CCTGCTGA        48

(2) INFORMATION FOR SEQ ID NO:66:

(i) SEQUENCE CHARACTERISTICS:
        (A) LENGTH: 15 amino acids
        (B) TYPE: amino acid
        (D) TOPOLOGY: linear (i i) MOLECULE TYPE: peptide (i i i) HYPOTHETICAL: NO (v i) ORIGINAL SOURCE:
        (A) ORGANISM: Homo sapiens (x i) SEQUENCE DESCRIPTION: SEQ ID NO:66:

Val Ile Tyr Arg Leu Ser Ser His Pro Thr Arg Leu Pro Ser Cys
1               5                   10                  15

(2) INFORMATION FOR SEQ ID NO:67:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i i i) HYPOTHETICAL: NO (v i) ORIGINAL SOURCE:
        (A) ORGANISM: Homo sapiens (x i) SEQUENCE DESCRIPTION: SEQ ID NO:67:

Leu Ile Ala His Trp Leu
1               5

(2) INFORMATION FOR SEQ ID NO:68:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i i i) HYPOTHETICAL: NO (x i) SEQUENCE DESCRIPTION: SEQ ID NO:68:

Leu Ile Val His Trp Leu
1               5

(2) INFORMATION FOR SEQ ID NO:69:

(i) SEQUENCE CHARACTERISTICS:
        (A) LENGTH: 6 amino acids
        (B) TYPE: amino acid
        (D) TOPOLOGY: linear (i i) MOLECULE TYPE: peptide (i i i) HYPOTHETICAL: NO (x i) SEQUENCE DESCRIPTION: SEQ ID NO:69:

Leu Ala Ala His Trp Lys
1               5

( 2 ) INFORMATION FOR SEQ ID NO:70:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:70:

Leu  Ala  Ala  His  Trp  Met
    1                         5

( 2 ) INFORMATION FOR SEQ ID NO:71:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:71:

Leu  Val  Ala  His  Trp  Leu
    1                         5

( 2 ) INFORMATION FOR SEQ ID NO:72:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:72:

Leu  Ala  Ala  His  Trp  Leu
    1                         5

( 2 ) INFORMATION FOR SEQ ID NO:73:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:73:

Asp  Ile  Leu  Ile  Asn  Phe  Arg
    1                         5

( 2 ) INFORMATION FOR SEQ ID NO:74:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:74:

Asp Ile Leu Ile Asp Phe Arg
1               5

( 2 ) INFORMATION FOR SEQ ID NO:75:

( i ) SEQUENCE CHARACTERISTICS:
       ( A ) LENGTH: 7 amino acids
       ( B ) TYPE: amino acid
       ( D ) TOPOLOGY: linear ( i i ) MOLECULE TYPE: peptide ( i i i ) HYPOTHETICAL: NO ( x i ) SEQUENCE DESCRIPTION: SEQ ID NO:75:

Asp Ile Val Leu Asn Phe His
1               5

( 2 ) INFORMATION FOR SEQ ID NO:76:

( i ) SEQUENCE CHARACTERISTICS:
       ( A ) LENGTH: 7 amino acids
       ( B ) TYPE: amino acid
       ( D ) TOPOLOGY: linear ( i i ) MOLECULE TYPE: peptide ( i i i ) HYPOTHETICAL: NO ( x i ) SEQUENCE DESCRIPTION: SEQ ID NO:76:

Asp Ile Leu Leu Asn Phe Arg
1               5

( 2 ) INFORMATION FOR SEQ ID NO:77:

( i ) SEQUENCE CHARACTERISTICS:
       ( A ) LENGTH: 8 amino acids
       ( B ) TYPE: amino acid
       ( D ) TOPOLOGY: linear ( i i ) MOLECULE TYPE: peptide ( i i i ) HYPOTHETICAL: NO ( v i ) ORIGINAL SOURCE:
       ( A ) ORGANISM: Homo sapiens ( x i ) SEQUENCE DESCRIPTION: SEQ ID NO:77:

Ser Val Gly Phe Gly Asn Val Ser
1               5

( 2 ) INFORMATION FOR SEQ ID NO:78:

( i ) SEQUENCE CHARACTERISTICS:
       ( A ) LENGTH: 8 amino acids
       ( B ) TYPE: amino acid
       ( D ) TOPOLOGY: linear ( i i ) MOLECULE TYPE: peptide ( i i i ) HYPOTHETICAL: NO ( x i ) SEQUENCE DESCRIPTION: SEQ ID NO:78:

Ser Val Gly Phe Ser Asn Val Ser
1               5

( 2 ) INFORMATION FOR SEQ ID NO:79:

( i ) SEQUENCE CHARACTERISTICS:

(A) LENGTH: 8 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:79:

Ser Val Gly Phe Gly Asn Ile Ala
        1               5

(2) INFORMATION FOR SEQ ID NO:80:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:80:

Ser Val Gly Phe Gly Asn Val Ala
        1               5

(2) INFORMATION FOR SEQ ID NO:81:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: NO (xi) SEQUENCE DESCRIPTION: SEQ ID NO:81:

Thr Val Gly Tyr Gly Asp Met Thr
        1               5